US010532154B2

(12) United States Patent
Prince et al.

(10) Patent No.: US 10,532,154 B2
(45) Date of Patent: *Jan. 14, 2020

(54) SELECTIVELY CONTROLLING FLUID FLOW THROUGH A FLUID PATHWAY

(71) Applicant: CRISI Medical Systems, Inc., Franklin Lakes, NJ (US)

(72) Inventors: Stephen M. Prince, La Jolla, CA (US); Walter J. Bochenko, Encinitas, CA (US); Winthrop De Childers, San Diego, CA (US)

(73) Assignee: CRISI Medical Systems, Inc., Franklin Lakes, NJ (US)

( * ) Notice: Subject to any disclaimer, the term of this patent is extended or adjusted under 35 U.S.C. 154(b) by 124 days.

This patent is subject to a terminal disclaimer.

(21) Appl. No.: 15/652,882

(22) Filed: Jul. 18, 2017

(65) Prior Publication Data
US 2017/0312429 A1   Nov. 2, 2017

Related U.S. Application Data

(63) Continuation of application No. 13/689,729, filed on Nov. 29, 2012, now Pat. No. 9,744,298, which is a
(Continued)

(51) Int. Cl.
*A61M 5/168* (2006.01)
*A61M 5/172* (2006.01)
*A61M 1/10* (2006.01)

(52) U.S. Cl.
CPC ........ *A61M 5/16881* (2013.01); *A61M 5/172* (2013.01); *A61M 1/1086* (2013.01);
(Continued)

(58) Field of Classification Search
CPC .............. A61M 5/168; A61M 5/16804; A61M 5/16827; A61M 5/16831; A61M 5/16836;
(Continued)

(56) References Cited

U.S. PATENT DOCUMENTS

| 3,430,625 A | 3/1969 | McLeod, Jr. |
| 4,003,252 A | 1/1977 | Dewath |

(Continued)

FOREIGN PATENT DOCUMENTS

| CN | 101732778 A | 6/2010 |
| CN | 102791310 A | 11/2012 |

(Continued)

*Primary Examiner* — Nilay J Shah
(74) *Attorney, Agent, or Firm* — The Webb Law Firm

(57) ABSTRACT

Systems and methods for controlling fluid delivery via a manually administrable medication container to a patient through a fluid delivery pathway are provided. The systems and methods described herein incorporate rules-based clinical decision support logic to drive a flow control valve within a flow pathway based on a determination of whether or not an IV fluid connected to an input port on the pathway is appropriate for patient administration by considering such factors as patient-specific clinical circumstances, current medical orders, and accepted delivery protocols. Related apparatus, systems, methods and articles are also described.

41 Claims, 10 Drawing Sheets

Related U.S. Application Data continuation-in-part of application No. 13/529,876, filed on Jun. 21, 2012, now Pat. No. 10,293,107.

(60) Provisional application No. 61/500,073, filed on Jun. 22, 2011.

(52) U.S. Cl.
CPC ........... *A61M 5/168* (2013.01); *A61M 5/1684* (2013.01); *A61M 5/16804* (2013.01); *A61M 5/16827* (2013.01); *A61M 5/16831* (2013.01); *A61M 5/16836* (2013.01); *A61M 5/16877* (2013.01); *A61M 5/16886* (2013.01); *A61M 5/1723* (2013.01); *A61M 2205/6009* (2013.01); *A61M 2205/6018* (2013.01); *A61M 2205/6054* (2013.01)

(58) Field of Classification Search
CPC ............ A61M 5/1684; A61M 5/16877; A61M 5/16881; A61M 5/16886; A61M 5/1723; A61M 1/1086
See application file for complete search history.

(56) References Cited

U.S. PATENT DOCUMENTS

| | | | |
|---|---|---|---|
| 4,415,802 A | 11/1983 | Long | |
| 4,650,475 A | 3/1987 | Smith et al. | |
| 4,657,490 A | 4/1987 | Abbott | |
| 4,684,367 A * | 8/1987 | Schaffer | A61M 5/1483 128/DIG. 12 |
| 4,759,527 A | 7/1988 | Brown et al. | |
| 4,853,521 A | 8/1989 | Claeys et al. | |
| 4,857,713 A | 8/1989 | Brown | |
| 4,921,277 A | 5/1990 | McDonough | |
| 4,978,335 A | 12/1990 | Arthur, III | |
| 5,011,032 A | 4/1991 | Rollman | |
| 5,040,422 A | 8/1991 | Frankenberger et al. | |
| 5,078,683 A | 1/1992 | Sancoff et al. | |
| 5,179,862 A | 1/1993 | Lynnworth | |
| 5,247,826 A | 9/1993 | Frola | |
| 5,279,576 A | 1/1994 | Loo et al. | |
| 5,317,506 A | 5/1994 | Coutre et al. | |
| 5,338,157 A | 8/1994 | Blomquist | |
| 5,383,858 A | 1/1995 | Reilly et al. | |
| 5,429,602 A | 7/1995 | Hauser | |
| 5,463,906 A | 11/1995 | Spani et al. | |
| 5,531,697 A | 7/1996 | Olsen et al. | |
| 5,531,698 A | 7/1996 | Olsen | |
| 5,569,212 A | 10/1996 | Brown | |
| 5,611,784 A | 3/1997 | Barresi et al. | |
| 5,612,524 A | 3/1997 | Sant'Anselmo et al. | |
| 5,628,309 A | 5/1997 | Brown | |
| 5,651,775 A | 7/1997 | Walker et al. | |
| 5,692,640 A | 12/1997 | Caulfield et al. | |
| 5,713,856 A | 2/1998 | Eggers et al. | |
| 5,720,733 A | 2/1998 | Brown | |
| 5,740,428 A | 4/1998 | Mortimore et al. | |
| 5,781,442 A | 7/1998 | Engleson et al. | |
| 5,782,814 A | 7/1998 | Brown et al. | |
| 5,792,117 A | 8/1998 | Brown | |
| 5,833,213 A | 11/1998 | Ryan | |
| 5,845,264 A | 12/1998 | Nellhaus | |
| 5,873,731 A | 2/1999 | Prendergast | |
| 5,882,338 A | 3/1999 | Gray | |
| 5,920,263 A | 7/1999 | Huttenhoff et al. | |
| 5,925,014 A | 7/1999 | Teeple, Jr. | |
| 5,941,846 A | 8/1999 | Duffy et al. | |
| 5,984,901 A | 11/1999 | Sudo et al. | |
| 6,019,745 A | 2/2000 | Gray | |
| 6,039,251 A | 3/2000 | Holowko et al. | |
| 6,106,498 A | 8/2000 | Friedli et al. | |
| 6,123,686 A | 9/2000 | Olsen et al. | |
| 6,192,945 B1 | 2/2001 | Ford et al. | |
| D438,634 S | 3/2001 | Merry | |
| 6,249,299 B1 | 6/2001 | Tainer | |
| 6,256,037 B1 | 7/2001 | Callahan | |
| 6,270,455 B1 | 8/2001 | Brown | |
| 6,277,099 B1 | 8/2001 | Strowe et al. | |
| 6,338,200 B1 | 1/2002 | Baxa et al. | |
| 6,341,174 B1 | 1/2002 | Callahan et al. | |
| 6,342,889 B1 | 1/2002 | Callahan | |
| 6,381,029 B1 | 4/2002 | Tipirneni | |
| 6,422,094 B1 | 7/2002 | Ganshorn | |
| 6,464,667 B1 | 10/2002 | Kamen et al. | |
| 6,468,424 B1 | 10/2002 | Donig et al. | |
| 6,471,089 B2 | 10/2002 | Liff et al. | |
| 6,482,185 B1 | 11/2002 | Hartmann | |
| 6,497,680 B1 * | 12/2002 | Holst | A61M 5/14224 604/153 |
| 6,519,569 B1 | 2/2003 | White et al. | |
| 6,579,231 B1 | 6/2003 | Phipps | |
| RE38,189 E | 7/2003 | Walker et al. | |
| 6,626,355 B2 | 9/2003 | Sasse et al. | |
| 6,626,862 B1 | 9/2003 | Duchon et al. | |
| D481,121 S | 10/2003 | Evans | |
| 6,641,562 B1 | 11/2003 | Peterson | |
| 6,644,130 B2 | 11/2003 | Imai et al. | |
| 6,671,563 B1 | 12/2003 | Engelson et al. | |
| D485,356 S | 1/2004 | Evans | |
| 6,675,660 B1 | 1/2004 | Mosier et al. | |
| 6,685,227 B2 | 2/2004 | Merry et al. | |
| 6,685,678 B2 | 2/2004 | Evans et al. | |
| 6,697,067 B1 | 2/2004 | Callahan et al. | |
| 6,731,989 B2 | 5/2004 | Engleson et al. | |
| 6,733,495 B1 | 5/2004 | Bek et al. | |
| 6,742,992 B2 | 6/2004 | Davis | |
| 6,790,198 B1 | 9/2004 | White et al. | |
| 6,798,533 B2 | 9/2004 | Tipirneni | |
| 6,825,864 B2 | 11/2004 | Botten et al. | |
| 6,851,615 B2 | 2/2005 | Jones | |
| 6,854,338 B2 | 2/2005 | Khuri-Yakub et al. | |
| 6,915,170 B2 | 7/2005 | Engleson et al. | |
| 6,960,192 B1 | 11/2005 | Flaherty et al. | |
| 6,985,870 B2 | 1/2006 | Martucci et al. | |
| 6,993,402 B2 | 1/2006 | Klass et al. | |
| 7,000,485 B2 | 2/2006 | Ao et al. | |
| 7,017,623 B2 | 3/2006 | Tribble et al. | |
| 7,061,831 B2 | 6/2006 | De La Huerga | |
| 7,074,205 B1 | 7/2006 | Duffy et al. | |
| 7,074,209 B2 | 7/2006 | Evans et al. | |
| 7,096,072 B2 | 8/2006 | Engleson et al. | |
| 7,103,419 B2 | 9/2006 | Engleson et al. | |
| 7,106,479 B2 | 9/2006 | Roy et al. | |
| 7,107,106 B2 | 9/2006 | Engleson et al. | |
| 7,115,113 B2 | 10/2006 | Evans et al. | |
| 7,116,343 B2 | 10/2006 | Botten et al. | |
| 7,117,041 B2 | 10/2006 | Engleson et al. | |
| 7,161,488 B2 | 1/2007 | Frasch | |
| 7,171,277 B2 | 1/2007 | Engleson et al. | |
| 7,175,081 B2 | 2/2007 | Andreasson et al. | |
| 7,180,624 B2 | 2/2007 | Tipirneni | |
| 7,182,256 B2 | 2/2007 | Andreasson et al. | |
| 7,225,683 B2 | 6/2007 | Harnett et al. | |
| 7,236,936 B2 | 6/2007 | White et al. | |
| 7,237,199 B1 | 6/2007 | Menhardt et al. | |
| 7,264,323 B2 | 9/2007 | Tainer et al. | |
| 7,299,981 B2 | 11/2007 | Hickle et al. | |
| 7,319,540 B2 | 1/2008 | Tipirneni | |
| 7,347,841 B2 | 3/2008 | Elhadad et al. | |
| 7,358,505 B2 | 4/2008 | Woodworth et al. | |
| 7,360,448 B2 | 4/2008 | Maginnis et al. | |
| 7,364,067 B2 | 4/2008 | Steusloff et al. | |
| 7,370,797 B1 | 5/2008 | Sullivan et al. | |
| 7,375,737 B2 | 5/2008 | Botten et al. | |
| 7,384,410 B2 | 6/2008 | Eggers et al. | |
| 7,442,181 B2 | 10/2008 | Schubert et al. | |
| 7,469,598 B2 | 12/2008 | Shkarlet et al. | |
| 7,469,599 B2 | 12/2008 | Froehlich et al. | |
| 7,470,266 B2 | 12/2008 | Massengale et al. | |
| 7,483,756 B2 | 1/2009 | Engleson et al. | |
| D588,200 S | 3/2009 | Langan et al. | |
| 7,534,239 B1 | 5/2009 | Schneider et al. | |

(56) References Cited

U.S. PATENT DOCUMENTS

| | | |
|---|---|---|
| D593,613 S | 6/2009 | Langan et al. |
| D595,361 S | 6/2009 | Langan et al. |
| 7,559,483 B2 | 7/2009 | Hickle et al. |
| 7,564,579 B2 | 7/2009 | Tipirneni |
| D597,608 S | 8/2009 | Langan et al. |
| D602,534 S | 10/2009 | Langan et al. |
| 7,614,545 B2 | 11/2009 | Christoffersen et al. |
| 7,617,739 B1 | 11/2009 | Dam |
| D605,228 S | 12/2009 | Langan et al. |
| D605,229 S | 12/2009 | Langan et al. |
| D605,230 S | 12/2009 | Langan et al. |
| 7,645,258 B2 | 1/2010 | White et al. |
| 7,673,527 B2 | 3/2010 | Ehring et al. |
| 7,694,565 B2 | 4/2010 | Koerdt et al. |
| 7,703,336 B2 | 4/2010 | Genosar |
| 7,704,231 B2 | 4/2010 | Pongpairochana et al. |
| 7,722,083 B2 | 5/2010 | McCarthy et al. |
| 7,727,196 B2 | 6/2010 | Neer |
| 7,753,880 B2 | 7/2010 | Malackowski |
| 7,753,891 B2 | 7/2010 | Tennican et al. |
| 7,756,724 B2 | 7/2010 | Gropper et al. |
| 7,763,006 B2 | 7/2010 | Tennican |
| D621,879 S | 8/2010 | Langan et al. |
| D621,880 S | 8/2010 | Langan et al. |
| 7,771,385 B2 | 8/2010 | Eggers et al. |
| D624,595 S | 9/2010 | Langan et al. |
| D624,596 S | 9/2010 | Langan et al. |
| 7,799,010 B2 | 9/2010 | Tennican |
| 7,813,939 B2 | 10/2010 | Clements et al. |
| 7,815,123 B2 | 10/2010 | Conner et al. |
| 7,815,605 B2 | 10/2010 | Souter |
| 7,819,838 B2 | 10/2010 | Ziegler et al. |
| 7,822,096 B2 | 10/2010 | Kuksenkov |
| 7,834,816 B2 | 11/2010 | Marino et al. |
| 7,859,473 B2 | 12/2010 | Gibson |
| D633,151 S | 2/2011 | Langan et al. |
| 7,887,513 B2 | 2/2011 | Nemoto et al. |
| D634,367 S | 3/2011 | Langan et al. |
| D634,368 S | 3/2011 | Langan et al. |
| D634,369 S | 3/2011 | Langan et al. |
| 7,905,861 B2 | 3/2011 | Rhinehart et al. |
| 7,918,830 B2 | 4/2011 | Langan et al. |
| 7,922,073 B2 | 4/2011 | De La Huerga |
| 7,927,313 B2 | 4/2011 | Stewart et al. |
| 7,933,780 B2 | 4/2011 | de la Huerga |
| 7,941,949 B2 | 5/2011 | Cloninger |
| D639,861 S | 6/2011 | Langan et al. |
| D639,862 S | 6/2011 | Langan et al. |
| D639,863 S | 6/2011 | Langan et al. |
| 7,967,778 B2 | 6/2011 | Nemoto et al. |
| D641,421 S | 7/2011 | Langan et al. |
| D641,422 S | 7/2011 | Langan et al. |
| 7,976,508 B2 | 7/2011 | Hoag |
| 7,981,073 B2 | 7/2011 | Mollstam et al. |
| D643,468 S | 8/2011 | Langan et al. |
| D643,469 S | 8/2011 | Langan et al. |
| D643,470 S | 8/2011 | Langan et al. |
| D643,471 S | 8/2011 | Langan et al. |
| D643,472 S | 8/2011 | Langan et al. |
| 7,991,627 B2 | 8/2011 | Hutchinson et al. |
| D645,094 S | 9/2011 | Langan et al. |
| 8,031,347 B2 | 10/2011 | Edwards et al. |
| 8,035,517 B2 | 10/2011 | Gibson |
| D649,196 S | 11/2011 | Langan et al. |
| 8,059,297 B2 | 11/2011 | Tipirneni |
| 8,063,925 B2 | 11/2011 | Tainer et al. |
| 8,065,924 B2 | 11/2011 | Ziegler et al. |
| 8,069,060 B2 | 11/2011 | Tipirneni |
| 8,111,159 B2 | 2/2012 | Andreasson et al. |
| 8,133,178 B2 | 3/2012 | Brauker et al. |
| 8,140,349 B2 | 3/2012 | Hanson et al. |
| 8,151,835 B2 | 4/2012 | Khan et al. |
| 8,235,938 B2 | 8/2012 | Eggers et al. |
| 8,240,550 B2 | 8/2012 | Steusloff et al. |
| 8,303,547 B2 | 11/2012 | Brown |
| 8,328,082 B1 | 12/2012 | Bochenko et al. |
| 8,355,753 B2 | 1/2013 | Bochenko et al. |
| 8,385,972 B2 | 2/2013 | Bochenko et al. |
| 8,394,053 B2 | 3/2013 | Bochenko et al. |
| 8,480,834 B2 | 7/2013 | Rice et al. |
| 8,505,809 B2 | 8/2013 | Steusloff et al. |
| 8,606,596 B1 | 12/2013 | Bochenko et al. |
| 8,636,202 B2 | 1/2014 | Keefe et al. |
| 8,639,521 B2 | 1/2014 | Eggers et al. |
| 8,639,525 B2 | 1/2014 | Levine et al. |
| 8,645,154 B2 | 2/2014 | Eggers et al. |
| 8,702,674 B2 | 4/2014 | Bochenko |
| 8,728,020 B2 | 5/2014 | Caleffi et al. |
| 8,752,088 B1 | 6/2014 | Harvey et al. |
| 2001/0020148 A1 | 9/2001 | Sasse et al. |
| 2001/0029608 A1 | 12/2001 | Hochman |
| 2001/0056258 A1 | 12/2001 | Evans |
| 2002/0040208 A1 | 4/2002 | Flaherty et al. |
| 2002/0077852 A1 | 6/2002 | Ford et al. |
| 2002/0088131 A1 | 7/2002 | Baxa et al. |
| 2002/0098598 A1 | 7/2002 | Coffen et al. |
| 2002/0099334 A1 | 7/2002 | Hanson et al. |
| 2002/0169439 A1 | 11/2002 | Flaherty |
| 2002/0177811 A1 | 11/2002 | Reilly et al. |
| 2002/0188259 A1 | 12/2002 | Hickle et al. |
| 2003/0012701 A1 | 1/2003 | Sangha et al. |
| 2003/0052787 A1 | 3/2003 | Zerhusen et al. |
| 2003/0055685 A1 | 3/2003 | Cobb et al. |
| 2003/0065537 A1 | 4/2003 | Evans |
| 2003/0088238 A1 | 5/2003 | Poulsen et al. |
| 2003/0135388 A1 | 7/2003 | Martucci et al. |
| 2003/0139701 A1 | 7/2003 | White et al. |
| 2003/0139706 A1 | 7/2003 | Gray |
| 2003/0140929 A1 | 7/2003 | Wilkes et al. |
| 2003/0141981 A1 | 7/2003 | Bui et al. |
| 2003/0160698 A1 | 8/2003 | Andreasson et al. |
| 2003/0164401 A1 | 9/2003 | Andreasson et al. |
| 2003/0174326 A1 | 9/2003 | Rzasa et al. |
| 2004/0051368 A1 | 3/2004 | Caputo et al. |
| 2004/0082918 A1 | 4/2004 | Evans et al. |
| 2004/0092885 A1 | 5/2004 | Duchon et al. |
| 2004/0103951 A1 | 6/2004 | Osborne et al. |
| 2004/0104271 A1 | 6/2004 | Martucci et al. |
| 2004/0105115 A1 | 6/2004 | Edwards et al. |
| 2004/0179051 A1 | 9/2004 | Tainer et al. |
| 2004/0179132 A1 | 9/2004 | Fujino et al. |
| 2004/0186437 A1 | 9/2004 | Frenette et al. |
| 2004/0193453 A1 | 9/2004 | Butterfield et al. |
| 2004/0204673 A1 | 10/2004 | Flaherty |
| 2004/0212834 A1 | 10/2004 | Edwards et al. |
| 2004/0238631 A1 | 12/2004 | Andreasson et al. |
| 2005/0055242 A1 | 3/2005 | Bello et al. |
| 2005/0059926 A1 | 3/2005 | Sage, Jr. et al. |
| 2005/0070978 A1 | 3/2005 | Bek et al. |
| 2005/0088306 A1 | 4/2005 | Andreasson et al. |
| 2005/0101905 A1 | 5/2005 | Merry |
| 2005/0106225 A1 | 5/2005 | Massengale et al. |
| 2005/0107923 A1 | 5/2005 | Vanderveen |
| 2005/0118048 A1 | 6/2005 | Traxinger |
| 2005/0151652 A1 | 7/2005 | Frasch |
| 2005/0151823 A1 | 7/2005 | Botten et al. |
| 2005/0154368 A1 | 7/2005 | Lim et al. |
| 2005/0165559 A1 | 7/2005 | Nelson |
| 2005/0182358 A1 | 8/2005 | Veit et al. |
| 2005/0277873 A1 | 12/2005 | Stewart et al. |
| 2005/0277890 A1 | 12/2005 | Stewart et al. |
| 2006/0032918 A1 | 2/2006 | Andreasson et al. |
| 2006/0065713 A1 | 3/2006 | Kingery |
| 2006/0079767 A1 | 4/2006 | Gibbs et al. |
| 2006/0079843 A1 | 4/2006 | Brooks |
| 2006/0102503 A1 | 5/2006 | Elhadad et al. |
| 2006/0116639 A1 | 6/2006 | Russell |
| 2006/0122577 A1 | 6/2006 | Poulsen et al. |
| 2006/0143051 A1 | 6/2006 | Eggers et al. |
| 2006/0144942 A1 | 7/2006 | Evans et al. |
| 2006/0178617 A1 | 8/2006 | Adams et al. |
| 2006/0190302 A1 | 8/2006 | Eggers et al. |
| 2006/0206356 A1 | 9/2006 | Vanderveen |
| 2006/0224125 A1 | 10/2006 | Simpson et al. |

(56) References Cited

U.S. PATENT DOCUMENTS

| | | |
|---|---|---|
| 2006/0226089 A1 | 10/2006 | Robinson et al. |
| 2006/0229551 A1 | 10/2006 | Martinez et al. |
| 2006/0253346 A1 | 11/2006 | Gomez |
| 2006/0258985 A1 | 11/2006 | Thibadeau |
| 2006/0265186 A1 | 11/2006 | Holland et al. |
| 2006/0270997 A1 | 11/2006 | Lim et al. |
| 2006/0287887 A1 | 12/2006 | Hutchinson et al. |
| 2007/0008399 A1 | 1/2007 | Botten et al. |
| 2007/0043335 A1 | 2/2007 | Olsen et al. |
| 2007/0060874 A1 | 3/2007 | Nesbitt et al. |
| 2007/0100316 A1 | 5/2007 | Traxinger |
| 2007/0134044 A1 | 6/2007 | Colbrunn et al. |
| 2007/0135765 A1 | 6/2007 | Miller et al. |
| 2007/0136218 A1 | 6/2007 | Bauer et al. |
| 2007/0166198 A1 | 7/2007 | Sangha et al. |
| 2007/0167919 A1 | 7/2007 | Nemoto et al. |
| 2007/0179448 A1 | 8/2007 | Lim et al. |
| 2007/0186923 A1 | 8/2007 | Poutiatine et al. |
| 2007/0187475 A1 | 8/2007 | MacLeod |
| 2007/0191787 A1 | 8/2007 | Lim et al. |
| 2007/0255199 A1 | 11/2007 | Dewey |
| 2007/0279625 A1 | 12/2007 | Rzasa et al. |
| 2007/0280710 A1 | 12/2007 | Tainer et al. |
| 2007/0293830 A1 | 12/2007 | Martin |
| 2007/0299421 A1 | 12/2007 | Gibson |
| 2008/0038128 A1 | 2/2008 | Haar |
| 2008/0045930 A1 | 2/2008 | Makin et al. |
| 2008/0051937 A1 | 2/2008 | Khan et al. |
| 2008/0061153 A1 | 3/2008 | Hickle et al. |
| 2008/0065016 A1 | 3/2008 | Peterson et al. |
| 2008/0071219 A1 | 3/2008 | Rhinehart et al. |
| 2008/0118141 A1 | 5/2008 | Sommer et al. |
| 2008/0125724 A1 | 5/2008 | Monroe |
| 2008/0191013 A1 | 8/2008 | Liberatore |
| 2008/0208042 A1 | 8/2008 | Ortenzi et al. |
| 2008/0234630 A1 | 9/2008 | Iddan et al. |
| 2008/0243054 A1 | 10/2008 | Mollstam et al. |
| 2008/0243088 A1 | 10/2008 | Evans |
| 2008/0255523 A1 | 10/2008 | Grinberg |
| 2008/0294108 A1 | 11/2008 | Briones et al. |
| 2008/0306439 A1 | 12/2008 | Nelson et al. |
| 2009/0018494 A1 | 1/2009 | Nemoto et al. |
| 2009/0030730 A1 | 1/2009 | Dullemen et al. |
| 2009/0036846 A1 | 2/2009 | Dacquay et al. |
| 2009/0043253 A1 | 2/2009 | Podaima |
| 2009/0069714 A1 | 3/2009 | Eichmann et al. |
| 2009/0069743 A1* | 3/2009 | Krishnamoorthy ............ A61M 5/1459 604/66 |
| 2009/0085768 A1 | 4/2009 | Patel et al. |
| 2009/0093774 A1* | 4/2009 | Wang ............ A61M 5/142 604/247 |
| 2009/0112178 A1 | 4/2009 | Behzadi |
| 2009/0112333 A1 | 4/2009 | Sahai |
| 2009/0113996 A1 | 5/2009 | Wang et al. |
| 2009/0126483 A1 | 5/2009 | Blendinger et al. |
| 2009/0126866 A1 | 5/2009 | Stenner et al. |
| 2009/0137956 A1 | 5/2009 | Souter |
| 2009/0143673 A1 | 6/2009 | Drost et al. |
| 2009/0149744 A1 | 6/2009 | Nemoto et al. |
| 2009/0156931 A1 | 6/2009 | Nemoto et al. |
| 2009/0157008 A1 | 6/2009 | Vitral |
| 2009/0159654 A1 | 6/2009 | Grimard |
| 2009/0200185 A1 | 8/2009 | Follman et al. |
| 2009/0209911 A1 | 8/2009 | Cabus et al. |
| 2009/0259176 A1 | 10/2009 | Yairi |
| 2009/0288497 A1 | 11/2009 | Ziegler et al. |
| 2009/0294521 A1 | 12/2009 | de la Huerga |
| 2009/0296540 A1 | 12/2009 | Gilbert et al. |
| 2009/0306620 A1 | 12/2009 | Thilly et al. |
| 2010/0022953 A1 | 1/2010 | Bochenko et al. |
| 2010/0022987 A1 | 1/2010 | Bochenko et al. |
| 2010/0036310 A1 | 2/2010 | Hillman |
| 2010/0036313 A1 | 2/2010 | Shener et al. |
| 2010/0065633 A1 | 3/2010 | Nelson et al. |
| 2010/0065643 A1 | 3/2010 | Leyvraz et al. |
| 2010/0076310 A1 | 3/2010 | Wenderow et al. |
| 2010/0095782 A1 | 4/2010 | Ferencz et al. |
| 2010/0114951 A1 | 5/2010 | Bauman et al. |
| 2010/0145165 A1 | 6/2010 | Merry |
| 2010/0152562 A1 | 6/2010 | Goodnow et al. |
| 2010/0153136 A1 | 6/2010 | Whittacre et al. |
| 2010/0174266 A1 | 7/2010 | Estes |
| 2010/0179417 A1 | 7/2010 | Russo |
| 2010/0185182 A1* | 7/2010 | Alme ............ A61M 5/14276 604/891.1 |
| 2010/0204659 A1 | 8/2010 | Bochenko et al. |
| 2010/0262002 A1 | 10/2010 | Martz |
| 2010/0280486 A1 | 11/2010 | Khair et al. |
| 2010/0286599 A1 | 11/2010 | Ziegler et al. |
| 2010/0305499 A1 | 12/2010 | Matsiev et al. |
| 2011/0009800 A1 | 1/2011 | Dam et al. |
| 2011/0009817 A1 | 1/2011 | Bennett et al. |
| 2011/0028937 A1 | 2/2011 | Powers et al. |
| 2011/0060198 A1 | 3/2011 | Bennett et al. |
| 2011/0093279 A1 | 4/2011 | Levine et al. |
| 2011/0111794 A1 | 5/2011 | Bochenko et al. |
| 2011/0112473 A1 | 5/2011 | Bochenko et al. |
| 2011/0112474 A1 | 5/2011 | Bochenko et al. |
| 2011/0137288 A1 | 6/2011 | Tallarida et al. |
| 2011/0152824 A1 | 6/2011 | DiPerna et al. |
| 2011/0152825 A1 | 6/2011 | Marggi |
| 2011/0152834 A1 | 6/2011 | Langan et al. |
| 2011/0160655 A1 | 6/2011 | Hanson et al. |
| 2011/0161112 A1 | 6/2011 | Keefe et al. |
| 2011/0166511 A1 | 7/2011 | Sharvit et al. |
| 2011/0176490 A1 | 7/2011 | Mehta et al. |
| 2011/0185821 A1 | 8/2011 | Genosar |
| 2011/0220713 A1 | 9/2011 | Cloninger |
| 2011/0224649 A1 | 9/2011 | Duane et al. |
| 2011/0251584 A1 | 10/2011 | Khot |
| 2011/0259954 A1 | 10/2011 | Bartz et al. |
| 2011/0264069 A1 | 10/2011 | Bochenko |
| 2011/0295191 A1 | 12/2011 | Injev |
| 2011/0313349 A1 | 12/2011 | Krulevitch et al. |
| 2011/0315611 A1 | 12/2011 | Fulkerson et al. |
| 2012/0004542 A1 | 1/2012 | Nemoto et al. |
| 2012/0004602 A1 | 1/2012 | Hanson et al. |
| 2012/0004637 A1 | 1/2012 | Krulevitch et al. |
| 2012/0006127 A1 | 1/2012 | Nielsen |
| 2012/0022458 A1 | 1/2012 | Oh et al. |
| 2012/0035535 A1 | 2/2012 | Johnson et al. |
| 2012/0037266 A1 | 2/2012 | Bochenko |
| 2012/0041355 A1 | 2/2012 | Edman et al. |
| 2012/0045295 A1 | 2/2012 | Sato |
| 2012/0065617 A1 | 3/2012 | Matsiev et al. |
| 2012/0073673 A1 | 3/2012 | Kameyama |
| 2012/0222468 A1 | 9/2012 | Nelson et al. |
| 2012/0226446 A1 | 9/2012 | Nelson et al. |
| 2012/0226447 A1 | 9/2012 | Nelson et al. |
| 2012/0287431 A1 | 11/2012 | Matsiev et al. |
| 2012/0323208 A1 | 12/2012 | Bochenko et al. |
| 2012/0325330 A1 | 12/2012 | Prince et al. |
| 2013/0018356 A1 | 1/2013 | Prince et al. |
| 2013/0105568 A1 | 5/2013 | Jablonski et al. |
| 2013/0135388 A1 | 5/2013 | Samoto et al. |
| 2013/0181046 A1 | 7/2013 | Fedorko et al. |
| 2013/0204227 A1 | 8/2013 | Bochenko et al. |
| 2013/0225945 A1 | 8/2013 | Prince et al. |
| 2013/0226137 A1 | 8/2013 | Brown |
| 2013/0327822 A1 | 12/2013 | Keefe et al. |
| 2014/0039383 A1 | 2/2014 | Dobbles et al. |
| 2014/0060729 A1 | 3/2014 | Smka et al. |
| 2014/0142975 A1 | 5/2014 | Keefe et al. |
| 2015/0204705 A1 | 7/2015 | Forster et al. |
| 2015/0211904 A1 | 7/2015 | Forster |

FOREIGN PATENT DOCUMENTS

| | | |
|---|---|---|
| DE | 4137837 C1 | 10/1992 |
| DE | 29617777 U1 | 12/1996 |
| EP | 1944709 A1 | 7/2008 |
| EP | 1980974 A2 | 10/2008 |
| EP | 2135630 A1 | 12/2009 |

(56) References Cited

FOREIGN PATENT DOCUMENTS

| | | | |
|---|---|---|---|
| GB | 2183046 | A | 5/1987 |
| GB | 2504288 | A | 1/2014 |
| GB | 2504295 | A | 1/2014 |
| GB | 2504297 | A | 1/2014 |
| JP | 5317421 | A | 12/1993 |
| JP | 2008517646 | A | 5/2008 |
| JP | 201266004 | A | 4/2012 |
| KR | 1020090025392 | A | 3/2009 |
| WO | 03063932 | A2 | 8/2003 |
| WO | 2009114115 | A1 | 9/2009 |
| WO | 2010144482 | A2 | 12/2010 |
| WO | 2011126485 | A1 | 10/2011 |
| WO | 2012034084 | A2 | 3/2012 |
| WO | 2012126744 | A1 | 9/2012 |
| WO | 2013096713 | A2 | 6/2013 |
| WO | 2014016311 | A1 | 1/2014 |
| WO | 2014016315 | A1 | 1/2014 |
| WO | 2014016316 | A1 | 1/2014 |

\* cited by examiner

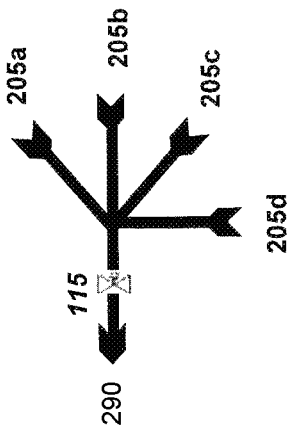
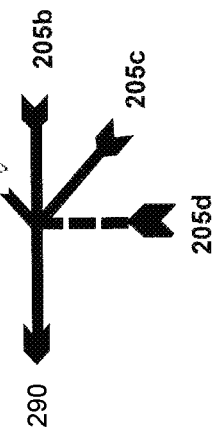
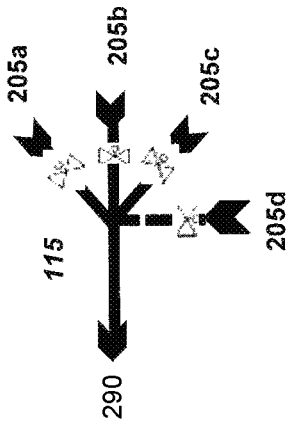
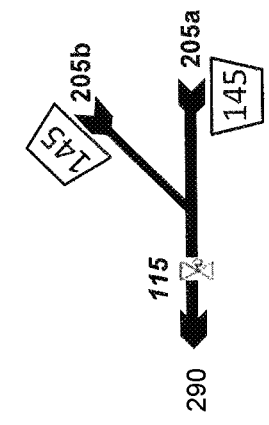
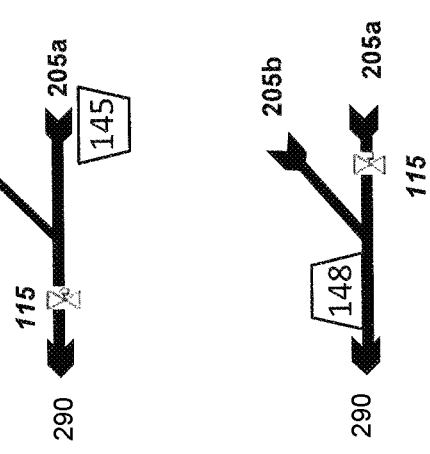
FIG. 2A   FIG. 2B   FIG. 2C   FIG. 2D   FIG. 2E   FIG. 2F   FIG. 2G

SELECTIVELY CONTROLLING FLUID FLOW THROUGH A FLUID PATHWAY

CROSS-REFERENCE TO RELATED APPLICATIONS

This application is a continuation of U.S. patent application Ser. No. 13/689,729 filed on Nov. 29, 2012, now U.S. Pat. No. 9,744,298, which is a continuation-in-part of U.S. patent application Ser. No. 13/529,876 filed on Jun. 21, 2012, now U.S. Pat. No. 10,293,107, which claims priority to U.S. Provisional Patent Application No. 61/500,073 filed on Jun. 22, 2011, the disclosures of each of which are hereby fully incorporated by reference.

FIELD

The subject matter described herein relates to systems and methods for controlling fluid flow to a patient through a fluid pathway.

BACKGROUND

There are a number of patient clinical settings including in-hospital, outpatient, in-home care and emergency medical services (EMS) that require fluid administration to a patient. Standard clinical best practice is to label fluids intended to be delivered to patients to reduce the potential for errors. However, mistakes in compatibility of fluids with a particular patient, incorrect dose measurements, inappropriate sequence of medications, incorrect transfer of labeling information and other factors continue to be major obstacles to overcome in providing safe patient care.

SUMMARY

The systems, apparatus, methods, and articles described herein provide mechanisms for preventing and/or mitigating patient fluid administration errors.

In one aspect, a system is provided that includes a fluid port, at least one sensor, a flow controller, and a flow control valve. The fluid port can include a fluid channel, a fluid inlet at a first end of the fluid channel configured to couple to an outlet of a manually administrable fluid source, and a fluid outlet at a second end of the fluid channel configured to deliver fluid from the manually administrable fluid source to a fluid pathway that provides fluid to a patient. The at least one sensor characterizes at least one attribute of the fluid from the manually administrable fluid source. The flow controller is in communication with the at least one sensor and generates at least one flow modification signal in response to the characterized at least one attribute matching at least one condition specified by at least one rule. The flow control valve is in communication with the flow controller and positioned along the fluid pathway at a location separate and distinct from the fluid port. The flow control valve changes a level of flow restriction of fluid from the manually administrable fluid source passing therethrough in response to receiving the at least one flow modification signal.

The at least one sensor can characterize at least one attribute of the fluid from the manually administrable fluid source (i) when the manually administrable fluid source is being coupled to the fluid inlet, (ii) when the manually administrable fluid source is coupled to the fluid inlet, and/or (iii) when fluid is passing through the fluid channel.

The at least one sensor can be integral or coupled to the fluid port. In other variations, the at least one sensor can be separate and distinct from the fluid port. In addition, multiple flow control valves at different points along the fluid pathway can be implemented in some variations. In addition, the flow control valve can be on the fluid pathway downstream from the fluid port and/or upstream from the fluid port.

Changing a level of flow restriction of fluid from the manually administrable fluid source passing through the flow control valve can include (i) stopping all fluid from passing through the flow control valve, and/or (ii) adjusting a current flow rate of fluid passing through the flow control valve to a higher or lower flow rate.

The flow controller can include or be in communication (e.g., via a computer network, via a wireless network, etc.) with a rules engine (which can be software and/or hardware implemented). Such a rules engine can use a plurality of rules to determine whether the at least one attribute matches the at least one condition specified by the at least one rule. The flow controller can, in some variations, poll at least one remote data source to obtain at least a portion of the rules. The rules engine, when applying the rules, can use (i) the at least one attribute, (ii) manually-entered user input, and (iii) flow control input data selected from a group consisting of: fluid information, patient-specific information, medical order information, clinical guideline information, environmental factors, flow control valve status, and historical information in order to determine whether there is a match for the at least one condition.

The fluid port can include a wireless transceiver for transmitting and receiving data to and from the flow controller, and the flow controller further comprises a wireless transceiver for transmitting and receiving data to and from the fluid port. In addition, the flow controller can transmit data to an external device other than the fluid port characterizing a state of the flow control valve.

The outlet of the manually administrable fluid source can include fluid source information encoded thereon. In such cases, the at least one sensor can include an identification sensor that detects the manually administrable fluid source information when the manually administrable fluid source is being coupled or is coupled to the fluid port inlet. The fluid source information can be a code or identifier used to reference a secondary data set that is characteristic of the fluid contained within the manually administrable fluid source. This secondary data set can be stored in memory (which can optionally form part of the fluid port). The secondary data set can be stored in a remote data source coupled to the flow controller via a communications network. The remote data source can form part of a medical device and/or a medical information system. The at least one flow modification signal can be generated using a rules engine that processes the detected fluid source information.

The at least one sensor can be a fluid composition sensor that characterizes a composition of fluid. The fluid composition sensor can be located along the fluid channel between the fluid inlet and fluid outlet. The at least one attribute can be indicative of at least one constituent present in fluid flowing through the channel. The at least one flow modification signal can be generated using a rules engine that processes the result of the sensed fluid composition information.

Contents from the manually administrable fluid source do not reach the patient for at least a time T1 after the manually administrable fluid source begins fluid delivery into the fluid inlet. To accommodate this arrangement, the flow controller and the flow control valve can be configured to restrict flow in the fluid pathway within a time T2<T1 after the manually administrable fluid source begins fluid delivery into to the fluid inlet.

Various elements forming part of the system may have wireless transmitters, receivers, and/or transceivers. A wireless transmitter can be provided to transmit data from the at least one sensor to the flow controller. A wireless transceiver can be coupled to the flow controller to receive and transmit data relating to operation of the flow control valve. A wireless receiver can be coupled to the flow control valve to receive a flow modification signal from the flow controller. A wireless transmitter can be coupled to the flow control valve to send information to the flow controller indicative of a change in the level of fluid flow restriction being applied to fluid passing through the flow control valve in response to receiving the at least one flow modification signal from the flow controller.

The at least one sensor can be any of a variety of sensors including identification sensors, flow sensors, and composition sensors.

The fluid can be a medication and the at least one attribute can characterize one or more: medication type, medication concentration, medication volume, medication expiration date, a dosage form of the medication, dose instructions for the medication, administration instructions for a specific patient, medication formulation, medication manufacturer information, a re-packager of the medication, a distributor of the medication, medication package form, medication package size, medication package serial number, medication lot number, blood type, an RxNorm identification code, an NDC code (National Drug Code), a segment of an NDC code identifying a corresponding medication product, a segment of an NDC code identifying a corresponding medication package, a unique identifier code, a human readable alphanumeric string, and a machine readable code.

The at least one flow modification signal can be automatically initiated and executed by the flow controller without user intervention. The at least one flow modification signal can be automatically initiated and executed by the flow controller as a result of coupling the outlet of the manually administrable fluid source to the fluid inlet and/or as a result of sensing the start of fluid flow into the fluid inlet.

An interface (e.g., display, GUI, etc.) can be included that provides audio and/or visual feedback to a user characterizing the at least one attribute and/or fluid contained within the manually administrable fluid source. The interface can provide an indication to the user of a state of the flow control valve. The interface can allow a user to input information to be used by the flow controller, in combination with information from the at least one sensor, to determine whether to generate the at least one flow modification signal. In cases in which the fluid is medication, the interface can display administration information and/or instructions associated with the medication. Such administration information and/or instructions can be stored within memory forming part of the system. A communications module can be provided to transmit and/or receive the administration information and/or instruction to/or from a remote data source. The interface can be adjacent to the fluid port or remote from the fluid port. The interface can display information about various aspects of fluid flow such as flow rate, composition, and the like.

A manual override element can be provided, which when activated by a user, causes the flow controller to cause the flow control valve to stop fluid flow in a first state or to allow fluid to flow in a second state.

A communications module can be provided to transmit and/or receive flow control input data, rules engine output data and/or data characterizing the fluid source to or from a remote data processing system.

There can be a plurality of fluid inlets such that each is configured to couple to an outlet of one of a plurality of manually administrable fluid sources. There can be a corresponding number of flow control valves that are coupled to the flow controller to selectively prevent fluid flowing from at least one of the plurality of fluid inlets.

The flow controller can receive data specifically relating to the patient that can be used, in combination with information from the at least one sensor and/or information manually-entered by the user, to determine whether to generate the at least one flow modification signal. Data relating to the patient can include at least one medication order. The at least one medication order can be used to confirm whether the fluid in the manually administrable fluid source matches the at least one condition specified by the at least one rule specified by the at least one medication order. The data characterizing the patient can include a patient identifier and the flow controller can poll at least one remote data store using the patient identifier to obtain reference information to determine whether to generate the at least one flow modification signal.

The at least one sensor can be a fluid flow sensor. Fluid flow information sensed by the fluid flow sensor can cause the flow controller to generate a first flow modification signal to cause the flow control valve to transition to a first state when a first pre-determined volume has been delivered as measured by the fluid flow sensor, and after a pre-determined span of time, cause the flow controller to generate a second flow modification signal to cause the flow control valve to transition to a second state different than the first state.

The at least one sensor can be an identification sensor that generates the at least one attribute using one or more technologies selected from a group including: optical, magnetic, mechanical, conductive, switchable, infrared, switchable RFID, and proximity sensors.

The at least one sensor can be a composition sensor that generates the at least one attribute using one or more technologies selected from a group including: photometric analysis, electrometric analysis, chromatography, mass spectroscopy, physical property measurements, or parametric analysis based on a combination of technologies.

The at least one sensor can be a fluid flow sensor that generates the at least one attribute using one or more technologies selected from a group including: a paddle wheel flow meter, a turbine flow meter, a thermal flow meter, an ultrasonic flow meter, a pressure sensor, a differential pressure sensor, an optical sensor, an ultrasonic sensor, a coriolis flow meter, a displacement sensor.

Some or all of the system can be enclosed by a housing. The housing can take different shapes and sizes. In some implementations, the housing envelopes at least a portion of each of the fluid inlet, the fluid outlet, the flow controller, and the at least one sensor. The housing can have a shape and size allowing a user to hold the housing in a first hand while coupling the manually administrable fluid source in a second hand. A self-contained power source can be provided within the housing to power the at least one sensor and/or other components. The fluid pathway can be an intravenous (IV) fluid line and the housing can be suspended on the IV fluid line.

The housing can include a reusable sub-housing and a disposable sub-housing. The reusable sub-housing can be operatively coupled to the disposable sub-housing and the reusable sub-housing is intended for use by a plurality of patients and the disposable sub-housing is intended for use by a single patient. In some variations, the at least the fluid inlet, fluid outlet, and flow channel can be enclosed by the disposable sub-housing. The disposable sub-housing can be included in a sterile pouch enveloping the disposable sub-housing. Memory can be placed within the disposable sub-housing for storing data used by the flow controller to determine whether to generate the at least one flow modification signal.

The manually administrable fluid source can be of any variety of medication containers/delivery mechanisms. Examples include, but are not limited to, syringes, IV bags, disposable medication cartridges, disposable medication pouches, and IV tubing.

In an interrelated aspect, a system includes a fluid port, at least one sensor, a controller, and a transmitter. The fluid port includes a fluid channel, a fluid inlet at a first end of the fluid channel configured to couple to an outlet of a manually administrable fluid source, a fluid outlet at a second end of the fluid channel configured to deliver fluid from the manually administrable fluid source to a fluid pathway that provides fluid to a patient. The at least one sensor characterizes at least one attribute of the fluid from the manually administrable fluid source. The controller is in communication with the at least one sensor and it generates at least one operation modification signal in response to the characterized at least one attribute matching at least one condition specified by at least one rule. The transmitter wirelessly transmitting the operation modification signal to at least one device such that the operation modification signal, when received by the at least one device, causes the at least one device to modify at least one operating parameter. With this variation, different types of devices can be used other than a flow controller (although the operation modification signal can also act to cause a flow controller to modify some parameter relating to fluid flow). For example, a medical device interacting with the fluid pathway can cause the fluid flow within the fluid pathway to be adjusted and/or other non-fluid flow operating parameters of a medical device can be modified.

In another variation, different types of external devices (e.g. infusion pumps, syringe pumps, etc.) can receive operation modification signals from the flow controller and take appropriate actions. For example, a medical device interacting with the fluid pathway can, in response to an operation modification signal, cause the fluid flow within the fluid pathway to be stopped. Alternatively, other non-fluid flow operating parameters of a medical device, such as the posting of an alert or the logging of a flow rate, can be modified (i.e. acted upon) based on receipt of an operation modification signal.

In a further interrelated aspect, data is received that is generated by at least one sensor of a fluid port characterizing at least one attribute of fluid within a manually administrable fluid source. The fluid port includes a fluid channel, a fluid inlet at a first end of the fluid channel configured to couple to an outlet of the manually administrable fluid source, and a fluid outlet at a second end of the fluid channel configured to deliver fluid from the manually administrable fluid source to a fluid pathway that provides fluid to a patient, and the at least one sensor. Thereafter, it can be determined that the at least one attribute in the received data matches at least one condition specified by at least one rule. In response, at least one flow modification signal is generated. The at least one flow modification signal, when received by a flow control valve, causes the flow control valve to change a level of fluid flow restriction being applied to fluid passing through the flow control valve.

In another aspect, an apparatus includes a fluid inlet, a fluid outlet, a flow control valve, an identification sensor, and a flow controller. The fluid inlet is configured to couple to an outlet of a manually administrable fluid source having fluid source information encoded thereon. The fluid outlet is configured to deliver fluid from the manually administrable fluid source to a fluid line (pathway) leading to a patient. The flow control valve is disposed between the fluid inlet and the fluid outlet that prevents fluid flow in a first state and permits fluid flow in a second state. The identification sensor is positioned to detect the fluid source information when the manually administrable fluid source is being coupled or is coupled to the fluid inlet. The flow controller selectively causes the flow control valve to transition between the first state and the second state based on the fluid source information detected by the identification sensor.

The flow controller can use a plurality of rules to determine whether to transition the current state of the flow control valve to the other state. Some or all of the rules can be obtained from a remote data source polled by the flow controller. A rules engine (i.e., software and/or hardware for applying the rules, etc.) can take into account the fluid source information, flow control input data, and one or more attributes of the patient and their history, clinical circumstances, environmental factors, clinical best practices and the like. The rules engine can be configurable and programmable according to one or more of user-inputted specifications (via for example, an interface on the apparatus or via a remote computing system/interface, etc.), patient specific data, and/or medication specific data.

A fluid composition sensor can be additionally incorporated to characterize a composition of the fluid when the manually administrable fluid source is coupled to the fluid inlet. In some cases, the fluid composition sensor can be used in place of the identification sensor while in other implementations it is used in combination with the identification sensor. In either arrangement, the flow controller can further selectively cause the flow control valve to transition between the first state and the second state based on the fluid composition detected by the fluid composition sensor.

The flow controller can transmit data characterizing the fluid source information detected by the identification sensor to a remote rules engine that sends a signal indicating whether to change a current state of the flow control valve. The fluid source information can be indicative of a characteristic of the fluid (e.g., medication, etc.) contained therein and can include one or more of an RxNorm identification code, NDC code (National Drug Code), a segment of the NDC code identifying the drug product, a segment of the NDC code identifying the drug package, a unique identifier code, a human readable alphanumeric string, a machine readable code, a name of the medication, a manufacturer of the medication, a re-packager of the medication, a distributor of the medication, a strength of the medication, a dosage form of the medication, dose instructions for the medication, administration instructions for a specific patient, medication formulation, medication package form, medication package size, medication contained volume, medication package serial number, medication lot number, and medication expiration date, fluid type, and blood type. The fluid source information can include a code or identifier used to reference a secondary data set that is characteristic of the fluid contained therein (i.e., a reference to a lookup table, a database object, a URL, etc.). The apparatus can include memory that stores the secondary data set locally and/or a remote data store can be coupled to the flow controller that stores the secondary data set. The remote data store can form part of a medical device or medical information system.

The transition between states can be automatically initiated and executed by the flow controller without user intervention. The transition between states can be automatically initiated and executed by the flow controller as a result of coupling the fluid source outlet to the fluid inlet.

An interface can be included to provide audio and/or visual feedback to a user characterizing one or more of the fluid source information, volume of fluid administration, rules engine information, and/or rules engine output. The interface can provide an indication to the user when the flow control valve is in the first state, an indication to the user of one or more rules used by a rules engine causing a flow control valve state transition, and/or an indication to the user without a flow control valve state transition. The interface can be adjacent to the fluid inlet and/or it can be remote from the fluid inlet (e.g., a display monitor wirelessly coupled to the flow controller, etc).

The interface can display medication administration information associated with the fluid. Such medication administration information can be stored on local memory. A communications module can be included to transmit and/or receive the medication administration information to or from a remote data source. The interface can be adjacent to or remote from the fluid inlet.

A manual override element, which when activated by a user, can cause the flow controller to cause the flow control valve to transition from the first state to the second state.

A communications module can be included to transmit and/or receive data to or from a remote data source characterizing one or more of the flow control input data, fluid source, the rules or a portion of the rules, and/or the patient.

In some implementations, there can be a plurality of fluid inlets that are each configured to couple to an outlet of one of a plurality of manually administrable fluid sources each having fluid source information thereon. In these arrangements, there can be a plurality of flow control valves that are each coupled to the flow controller to selectively prevent fluid flow in at least one of the plurality of fluid inlets.

The flow control valve can be maintained in the first state until it is determined, by using the fluid source information, to transition the flow control valve to the second state. The flow control valve can be maintained in the second state until it is determined, by using the fluid source information, to transition the flow control valve to the first state. The flow controller can receive data characterizing the patient that is used, in combination with the fluid flow source information, to determine whether to transition the current state of the flow control valve. The data characterizing the patient can include, for example, a medication order that is used to confirm whether the fluid in the fluid source matches one or more parameters specified by the at least one medication order. The data characterizing the patient can include a patient identifier that the flow controller uses to poll at least one remote data store using the patient identifier to obtain reference information for the flow controller to determine whether to transition the current state of the flow control valve.

A fluid flow sensor can be utilized that measures how much fluid has been delivered from the fluid source into the fluid inlet. The flow controller can cause the flow control valve to transition from the second state to the first state when a pre-determined volume has been delivered as measured by the fluid flow sensor. An interface can provide audio and/or visual feedback indicating how much fluid has been delivered as measured by the fluid flow sensor. The flow controller can cause the flow control valve to transition from the second state to the first state when a first predetermined volume has been delivered as measured by the fluid flow sensor, and after a pre-determined span of time, can cause the flow control valve to transition from the first state to the second state. The rules can utilize flow control input data information such as fluid information, patient-specific information, medical order information, clinical guideline information, contraindications, environmental factor information including time, flow control valve status, and historical information.

The identification sensor can detect the fluid source information using one or more technologies selected from a group consisting of: optical, magnetic, mechanical, conductive, switchable, infrared, switchable RFID and proximity sensors. In some cases, the identification sensor includes an optical element which detects an identifier encoded on a tip/outlet of the manually injectable medication container.

A housing can envelope at least a portion of each of the fluid inlet, the fluid outlet, the flow control valve, the identification sensor, and the flow controller. Such a housing can have a compact form/shape and size that allows a user to hold the housing in a first hand while activating the manually injectable medication container in a second hand. The housing can also include a self-contained power source within the housing powering the flow control valve, the identification sensor, and the flow controller and the fluid line can be an intravenous (IV) fluid line. The compact housing can, for example, be suspended from the IV fluid line.

The housing can be subdivided into reusable sub-housing and a disposable sub-housing. The reusable sub-housing can be operatively coupled to the disposable sub-housing with the reusable sub-housing being intended for use by a plurality of patients and the disposable sub-housing being intended for use by a single patient. The disposable sub-housing can contain at least the fluid inlet, fluid outlet, flow channel, and flow control valve. The disposable sub-housing can be part of a kit including a sterile pouch enveloping the disposable sub-housing. The disposable sub-housing can include memory for storing data that can include flow stop configuration information, flow sensor calibration information and/or a serial number or a unique identification number.

In an interrelated aspect, fluid source information of a manually administrable fluid source is detected by an identification sensor of a fluid delivery device, Thereafter, it is determined, using the detected fluid source information, whether to transition the current state of the flow control valve to the other state. A flow controller of the fluid delivery device then causes a flow control valve to transition to the other state (e.g., open or closed) if it is determined that the flow control valve should transition to the other state. Otherwise, the current state of the flow control valve is maintained if it is not determined that the flow control valve should transition to the other state.

In another variation a self-contained fluid port includes a fluid inlet for receiving manually administered medication, a fluid outlet for delivering the manually administered medication to a tubing segment leading to a patient, one or more sensors that sense one or more aspects of the injection of the medication, and electronics that wirelessly communicate the sensor information to external electronics. The one or more sensors may include one or more of a fluid source identification reader, a composition sensor, and a fluid flow sensor. The self-contained fluid port may be one integrally housed unit or it can include an electronics portion and a fluid portion. The electronics portion includes the electronics and may include a sensor such as a reader. The fluid portion may also include a fluid flow sensor.

In another variation, a fluid flow arrestor (flow control valve) can be physically separated from the self-contained fluid injection port and/or the fluid identification sensor and/or the fluid composition sensor. The fluid flow arrestor can be located upstream or downstream of the fluid injection port. The fluid flow arrestor can be within an external device like an infusion pump. A flow controller and/or a rules engine can be included to determine the appropriate state of the fluid flow arrestor (open or closed). The flow control valve can be responsive to a command from the flow controller and/or rules engine based on information provided by the fluid identification sensor and/or the fluid composition sensor. The flow control valve can be wirelessly connected or wired to the flow controller. The flow control valve can control the flow rate in a binary manor (open or closed) or it can restrict flow and limit the flow rate to a specific level. The flow controller and/or the rules engine can be external to the system and/or be distributed across several system elements. If distributed, the logic could cascade across systems (e.g.: if an outside rule is met AND an inside rule is met, THEN a trigger flow control command can be activated). The flow control valve can be powered by a self contained power source or connected to an external power source. The flow control valve can be a one-time activated device or can be resettable enabling repeat activation. The flow controller command signal can be published as an open-source such that any appropriate command could activate the flow control valve.

In another variation, the flow control valve can be part of a system to protect a patient from an inappropriate fluid administration. The system can include fluid flow paths with known volumes and flow rates. When a known volume of fluid is injected into a flowing fluid pathway the time for the injected fluid to reach the patient can be calculated. The flow control valve can be activated before the inappropriate fluid can reach the patient. A safety confirmation of fluid stop can be provided to the patient caregivers. Additionally, the fluid volume downstream from the injection port can be measured by fluid withdrawal into a syringe (pulling on an empty syringe connected to the injection port and withdrawing fluid into the syringe) with the upstream fluid pathway occluded (pinched off). The withdrawn downstream fluid volume can be measured manually by inspection of the syringe graduations or measured automatically by a fluid volume measurement sensor within the injection port apparatus. The measured downstream volume can be communicated to and stored in the rules engine. The downstream volume can then be used as an input to the flow controller.

In yet another variation, the fluid flow arrestor can include and/or be distributed between a disposable subsection and a reusable subsection. The interface between these subsections can be electrical, magnetic, mechanical, hydraulic, optical, capacitive. The disposable subsection can include the flow control valve only and the reusable subsection can include all the other components. Alternatively, the disposable subsection can include all the components including the flow control valve, power supply, wireless or wired communications and fluid path. In one variation, the disposable subsection includes portions of the fluid flow arrestor that are contacted with fluid and the reusable subsection includes portions of the fluid flow arrestor that do not contact fluid in order to minimize an expense of replacing the reusable subsection.

Computer program products are also described that comprise non-transitory computer readable media storing instructions, which when executed by at least one data processor of one or more computing systems, causes the at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. For example, the rules engine can be software-based or a combination of software-hardware based.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed embodiments. In the drawings:

FIGS. 2A-2G are diagrams illustrating alternative configurations of a fluid delivery pathway having one or more flow control valves and sensors;

Like reference symbols in the various drawings indicate like or similar elements.

DETAILED DESCRIPTION

Figure 1:
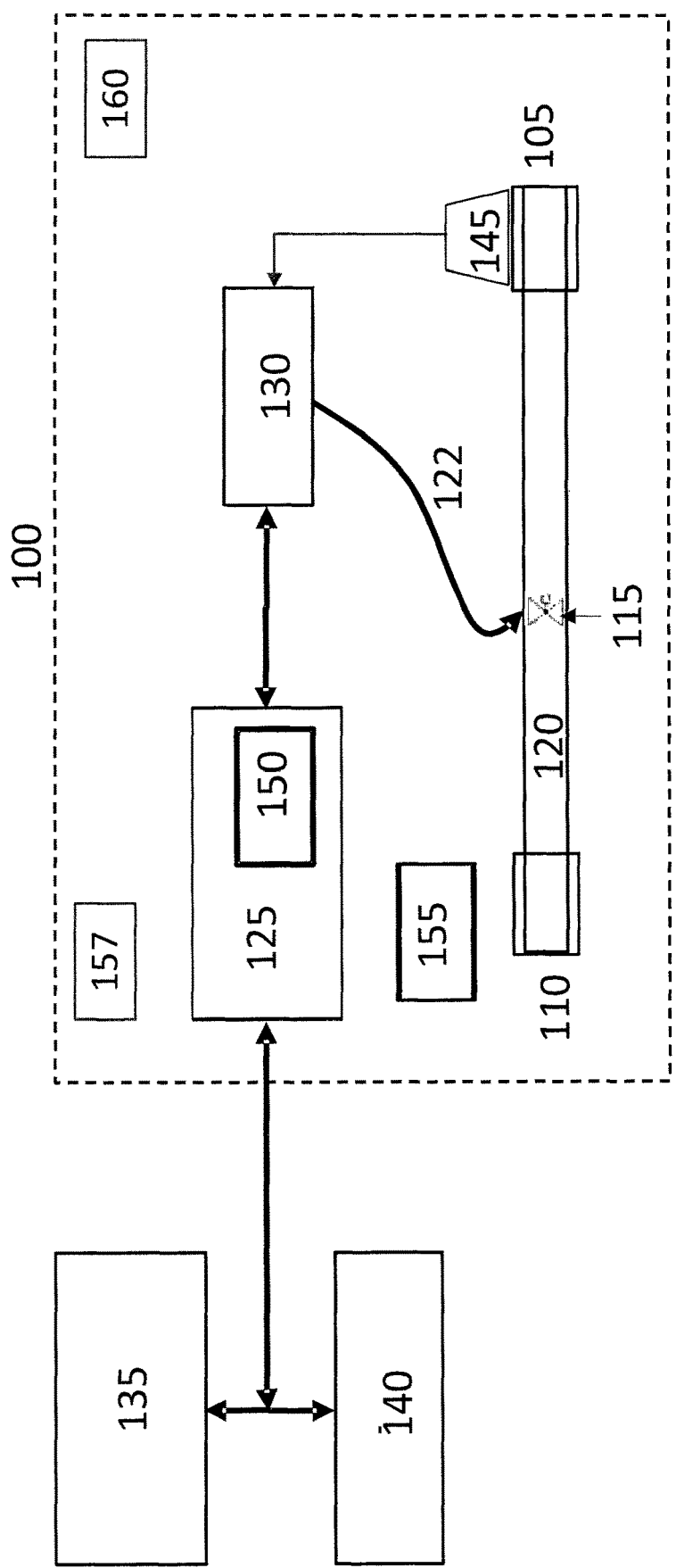
FIG. 1 is a diagram illustrating a system for controlling flow in a fluid delivery pathway.

Described herein are systems and methods for controlling fluid delivery to a patient through a fluid delivery pathway. The systems and methods described herein incorporate rules-based clinical decision support logic to drive a flow control valve along a fluid flow pathway leading to patient based on a determination of whether or not a fluid connected to an input port is appropriate for delivery to a specific patient (consistent with medical orders, accepted delivery protocols, patient-specific characteristics, etc.). In an alternative configuration, decision logic used to control the flow valve along the fluid pathway can be based on whether or not a specific volume of fluid has been delivered through the input port to the patient, rather than, or in addition to, a determination that the fluid is appropriate for patient administration.

Independent of the rules and flow-stop criteria used to actuate the flow control valve, the flow control valve can be physically located anywhere along the fluid pathway, including but not limited to within the fluid port itself, such that closure of the flow control valve will prevent fluid entering the fluid port from reaching the patient. Moreover, the flow control valve can be an integral part of the systems described herein, or it can be associated with an external device and/or system (e.g. infusion pump, wireless, IV tubing clamp, etc.) that actuates the valve in response to a trigger signal received from the systems described herein.

It should be appreciated that use of the term "fluid" herein is not limited to any specific fluid and can include any type of therapeutic fluid. Fluids as used herein can include, but are not limited to medications, blood-based products, nutritional solutions, electrolytes, buffer solutions, lactated Ringer's solutions, sodium bicarbonate, crystalloids, colloids, saline solutions. Blood-based products can include, but are not limited to, any component of the blood for use in blood transfusions, whole blood, fresh frozen plasma, cryoprecipitate, blood substitutes, artificial blood, oxygen-carrying substitutes. Medications can include any therapeutic fluid that can be administered intravenously or via another appropriate parenteral route of administration such as intra-arterial, intraosseous, intracerebral, intracardiac, subcutaneous, or intraperitoneal.

It is standard practice to query patients and place in the patient file medical record information such as blood type, known drug allergies, drugs patient is currently taking, dietary restrictions, etc. This data provides a caregiver with information regarding potential adverse reactions a particular patient may experience upon administration of such fluids. In an in-hospital setting this patient-specific information typically is entered into an Admission, Discharge and Transfer (ADT) system or other clinical documentation system when the patient is first admitted to the hospital and used throughout their length of stay to help ensure safe care. Clinical guidelines and best practices also support a host of non-patient-specific medical information that can be routinely taken into consideration by prescribers of IV medications/fluids such that administering clinicians can avoid inducing patient adverse events. This information can include, but is not limited to drug-drug interactions, blood type matching, appropriate drug dosing limits, impact of current vital signs on treatments, metabolic factors and/or lab results.

Fluids can be delivered according to a medical order defined by a prescribing physician. Delivery orders can specify information such as type of fluid, medication dose, frequency of dose, administration route, etc. In an in-hospital setting these orders can originate from and/or be accessible through a Computerized Physician Order Entry (CPOE) system, Pharmacy Information System (PIS), Blood Bank Information System (BBIS), or Operating Room Information System (ORIS). Safe delivery of medications or other fluids to patients can require clinicians to execute according to the prescribed medical orders, while simultaneously taking into consideration patient-specific health characteristics (e.g. blood type) and history (e.g. medications previously administered, allergies), drug-specific clinical guidelines, and a host of environmental circumstances such as current vital signs, time, etc.

Figure 7:
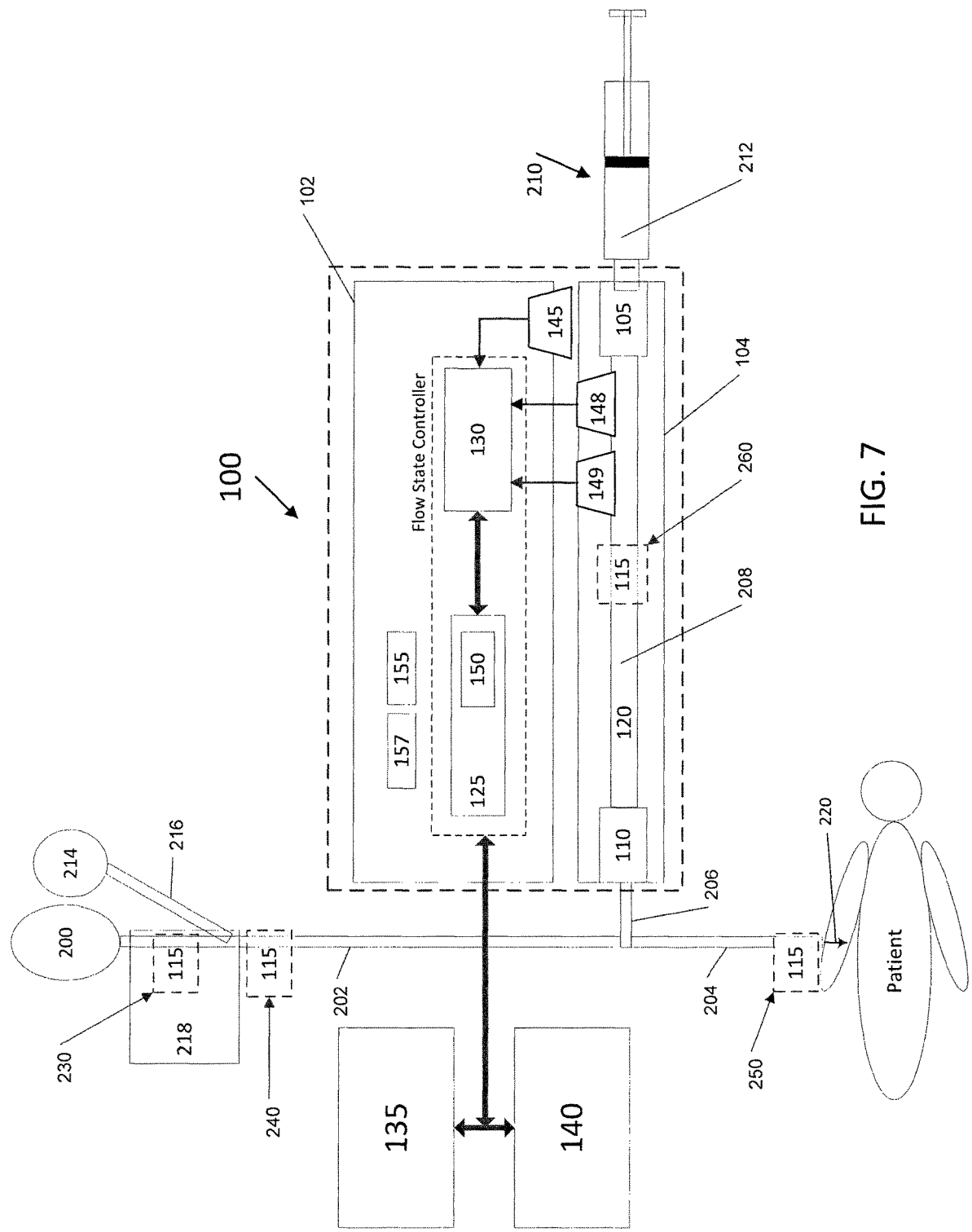
FIG. 7 is a diagram illustrating a physically separated flow control valve in various positions on the fluid delivery tubing in FIG. 6.

Turning now to FIG. 1, the system 100 can include a fluid delivery inlet 105 connected to a fluid delivery outlet 110 and one or more programmable flow control valves 115 (flow control valves) positioned within a fluid flow pathway 120 between the inlet 105 and the outlet 110. The system 100 can include a microprocessor 125 that interacts bi-directionally with a configurable rules engine 130. The configurable rules engine 130 can send flow state commands 122 to the flow control valve 115 in the fluid flow pathway 120. The microprocessor 125 also can communicate with an internal memory 150 and be powered by a power source 155. The system 100 also can include a transmitter/receiver 157. As shown in FIG. 7 (described further in a later section), one or more flow control valves 115 can reside external to fluid flow pathway 120 in a number of alternative fluid tubing locations, each having a flow path leading to the patient.

The microprocessor 125 can communicate with one or more external systems 135. Communication between the system 100 described herein and the one or more external systems 135 can include wired or wireless communication methods. The nature of the one or more external systems 135 can be in the form of tangible medical devices and/or systems such as IV infusion pumps, or software applications, including but not limited to, healthcare information systems such as PIS, BBIS, ORIS, or ADT systems. The system 100 can include a fluid source reader 145 coupled to the inlet 105 and configured to detect one or more information sources carried by the fluid source connected to the inlet 105. Information detected by the fluid source reader 145 can be indicative of a characteristic of the fluid contained within the associated fluid source container, such as type, volume, concentration, expiration, manufacturer's information regarding contents, etc. The information can be detected by the fluid source reader 145 according to a variety of methods, including but not limited to, optical, magnetic, mechanical, conductive, switchable, proximity sensors, IrDA, RFID, etc. Communication systems between inlets, fluid source readers and fluid source identification systems are described in detail in U.S. Patent Publication Nos. 2011/0112473, filed Nov. 6, 2009; 2011/0111794, filed Apr. 22, 2010; and 2011/0112474, filed Nov. 2, 2010, which are each incorporated by reference herein in their entirety.

The communication between the microprocessor 125 and the one or more external systems 135 can be bi-directional such that the microprocessor 125 can both receive and transmit flow control input data 140. Flow control input data 140 can include, but are not limited to, 1) information about the fluid source such as type of fluid, volume of fluid, concentration of fluid, etc.; 2) constant patient-specific information such as patient identification number, drug allergies, blood type, etc.; 3) variable patient-specific information such as patient vital signs, lab results, current disease states and/or clinical diagnoses, drugs previously administered, etc.; 4) medical orders such as drug, dose, route of administration, treatment schedule, etc.; 5) clinical guidelines such as known drug-drug interactions, recommended treatment protocols, dosing limits, etc.; 6) environmental factors such as the care area where treatment is being delivered, time of day, date, temperature, etc.; 7) valve status such as currently open (second state), currently closed (first state) or clinician initiation of a manual override; 8) historic patient information such as disease state, clinical diagnosis, dosing history, etc.; and 9) any other relevant information applicable to determining whether or not a particular fluid administration is safe and appropriate for a patient. Communication between the system 100 and the one or more external systems 135 is discussed in more detail below.

The systems described herein are generally small and light-weight systems that can reduce the risk of serious medical errors and deaths by controlling flow through a fluid delivery pathway. It should be appreciated that the systems described herein can be applied to any care environment where fluids are delivered to patients, including hospitals, clinics, outpatient surgery centers, doctor's offices, home health settings, EMS, ambulances, etc.

The system 100 described herein can be enclosed by a small plastic housing such that fluid inlet 105 and outlet 110 are available for external connections. The housing can enclose the fluid flow path 120, one or more flow control valves 115, and a power source 155. The housing can additionally enclose one or more of a microprocessor 125, a memory 150, a transmitter/receiver 157, a rules engine 130, a fluid source reader 145, and a fluid flow sensor 149 and/or composition sensor 148 (described later). The housing can be a low-cost, single-patient use, sterile, disposable assembly. Alternatively, the housing can include most or all of the system components and be reusable and rechargeable. System 100 can include a user interface 160, located adjacent to the fluid inlet or remote from the fluid inlet, to provide information to/from a user regarding a fluid and/or medication, audio/visual feedback, status of the flow stop valve 115 and other care related details. Any one or more of the components of the system 100 can be included or excluded from the housing in any number of alternative implementations.

In some implementations, system 100 can be subdivided and have components distributed such that a portion resides within a disposable sub-housing and the remainder resides outside the disposable sub-housing. The disposable sub-housing 104 (see FIG. 6) can be packaged sterile and be provided in a protective pouch. In one variation, for example, a first reusable sub-housing 102 (see FIG. 6) enclosing a power source 155, a microprocessor 125, a memory 150, a transmitter/receiver 157, a rules engine 130, and a fluid source reader 145 can mate with and attach to a second disposable sub-housing 104 enclosing a fluid flow pathway 120 and a flow control valve 115. Additionally, the disposable sub-housing 104 can include a subset of memory 150 storing characteristics of the components within the disposable sub-housing 104 relevant for proper operation (e.g. flow path characteristics, number of fluid inlets, number and arrangement of flow control valves, serial number, etc.) when the disposable and reusable sub-housings are combined to form a complete system 100.

As mentioned above, the system 100 can include a flow control valve 115 positioned within the fluid flow pathway 120 between the inlet 105 and the outlet 110. The flow control valve 115 can be a programmable valve that can toggle between two states in response to flow state commands 122 from the configurable rules engine 130. Flow control valve 115 can be limited to two operating modes, the first being an all-on "OPEN" state and the second being an all-off "CLOSED" state. Alternatively, flow control valve 115 can have multiple operating modes, including but not limited to, variable and intermittent flow control modes. Specific types of valves used can include, but are not limited to, gate valves, globe valves, T valves, butterfly valves, ball valves, check valves, plug valves, pinch valves, diaphragm valves, and the like.

FIG. 1 illustrates one of many potential component configurations (see FIG. 7 for possible alternate configurations) wherein a single flow control valve 115 can be positioned upstream from a single fluid outlet 110 and downstream from a single fluid inlet 105. FIGS. 2A-2G illustrate various alternative variations wherein one or more flow control valves 115 can be positioned within one or more tubing segments of fluid flow pathway 120, wherein such tubing segments are collectively referred to as a fluid administration "set", regardless of configuration. The fluid delivery pathway 120 can have a variety of configurations consistent with commonly used fluid administration sets including, for example, fluid flow pathway 120 configured as a single flow path extension set (FIG. 2A), a "Y-site" fluid set (FIGS. 2B-2D), a multiple-input to single-output fluid set (e.g. triple lumen IV catheter) (FIGS. 2E-2G), upstream or downstream from the fluid port as shown in FIG. 7 and others as are known in the art.

A flow control valve 115 can be positioned within a single fluid flow pathway 120 between an input fluid connector 205a and an output fluid connector 290 (see FIG. 2A). The flow control valve 115 can be positioned within the single fluid flow pathway 120 downstream of the Y-site with input 205b (see FIG. 2B). The flow control valve 115 can be positioned within the single fluid flow pathway 120 upstream of the Y-site with input 205b near input 205a (see FIG. 2C). The flow control valve 115 can be positioned within the Y-site near input 205b (see FIG. 2D). The flow control valve 115 can be positioned within a single fluid flow pathway 120 upstream of output fluid connector 290 and downstream of multiple-inputs 205a, 205b, 205c, 205d (see FIG. 2E). The flow control valve 115 can be positioned upstream of the single fluid flow pathway 120 and downstream of one or more of the multiple-inputs 205a, 205b, 205c, 205d (see FIGS. 2F and 2G).

Similarly, the fluid source reader 145 (and/or composition sensor 148) can be positioned on various segments of the fluid flow pathway 120 depending on the configuration of the components in the set. In some implementations, the fluid source reader 145 can be positioned in an upstream location along the same flow path as the flow control valve 115 (FIG. 2A). In some implementations, the fluid source reader 145 can be positioned along a different portion of the fluid flow pathway 120 as the flow control valve 115. For example, in a "Y-site" configuration such as shown in FIG. 2B, the flow control valve 115 can be positioned within the single fluid flow pathway 120 upstream of output fluid connector 290 and downstream of the Y-site. In this implementation, the fluid source reader 145 can be positioned upstream of the flow control valve 115 in the same fluid flow pathway 120 or a different flow path upstream of the Y-site. The fluid source reader 145 can also be positioned upstream of the flow control valve 115 in the same fluid flow pathway 120 downstream of the Y-site. Alternately, composition sensor 148 (or fluid source reader 145) can be positioned downstream of the Y-site as shown in FIG. 2C or positioned upstream on the Y-site as shown in FIG. 2D. Any number of component position combinations can be constructed for specific applications.

Figure 3:
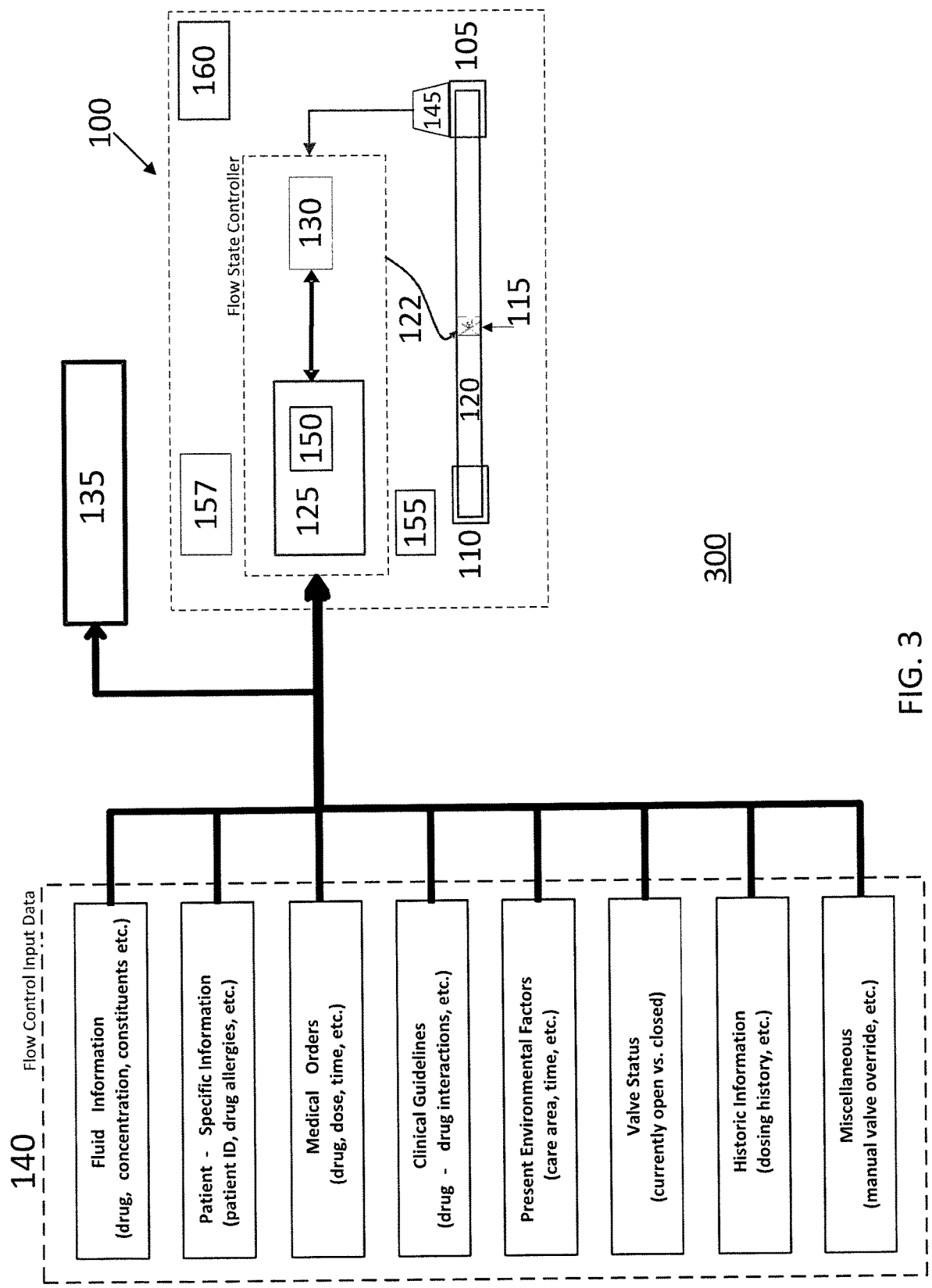
FIG. 3 is a diagram illustrating examples of flow control input data for the system of FIG. 1.

The microprocessor 125 can include a flow control valve software application in combination with rules engine 130 that evaluates combinations of flow control input data 140 against configurable logic for determining the proper state of the flow control valve 115 at any given time prior to or during a treatment regimen or fluid delivery protocol (see the diagram 300 of FIG. 3). Microprocessor 125, rules engine 130 and any associated flow control valve software application and/or configurable rules used by the rules engine 130 can sometimes be collectively referred to as a "flow controller". Access to the relevant flow control input data 140 allows the system 100 to support, guide, dictate, or perform clinical decisions relating to whether or not a particular fluid coupled to the system 100 should be allowed to flow through the fluid flow pathway 120 to a patient. As described above, the flow control input data 140 can be any data, whether patient-specific or non-patient-specific applicable to determining, for example, whether or a not a particular fluid administration is safe and appropriate for a patient. The data 140 can be stored in a medical information system, medical database, manually entered, input from an external device and/or system (e.g. vital signs monitor, laboratory information system, temperature sensor, etc.) or based on feedback from the system 100 or external system 135. The data 140 can be static or dynamic. Generally, the data 140 are applicable to and can provide support for making decisions on the appropriateness and/or safety of delivering a fluid to a patient.

The system 100 can be configured to operate in different operative modes. In some implementations, the system 100 can operate in a normally CLOSED mode where the baseline state of the flow control valve 115 is closed (first state) and the fluid flow pathway 120 is opened during a fluid delivery and then closed again upon completion of the delivery (see FIG. 4). The normally CLOSED mode can be advantageous in higher risk scenarios, for example, in instances in which a caregiver is less experienced or has limited decision-making authority regarding delivery of care; fluid administrations that requires more checks, involves fluid delivery of higher cost treatments, or administration of fluid treatments where mistakes have dire consequences such as infusion of incompatible blood products; or where highly potent and/or toxic substances (e.g. chemotherapy) are involved. In other implementations, the system 100 also can operate in a normally OPEN mode where the baseline state of the flow control valve 115 is open (second state) and closes only when there is an identified potential safety risk (see FIG. 5). The normally OPEN mode can be desirable or advantageous in scenarios such as, for example, instances in which a caregiver is more experienced or desires more manual control over fluid delivery, or the fluid administration and time-frame requires fewer checks. It should be appreciated that the system 100, regardless of operating mode, can include a manual override mechanism such that at any time during a particular fluid administration the clinician can override the system and force flow control valve 115 to an OPEN state allowing them to perform a conventional fluid administration as if the system 100 were not in place in the patient fluid line. The override mechanism can be reset manually by the clinician or automatically by the flow controller based on a timeout or other applicable rule.

Figure 4:
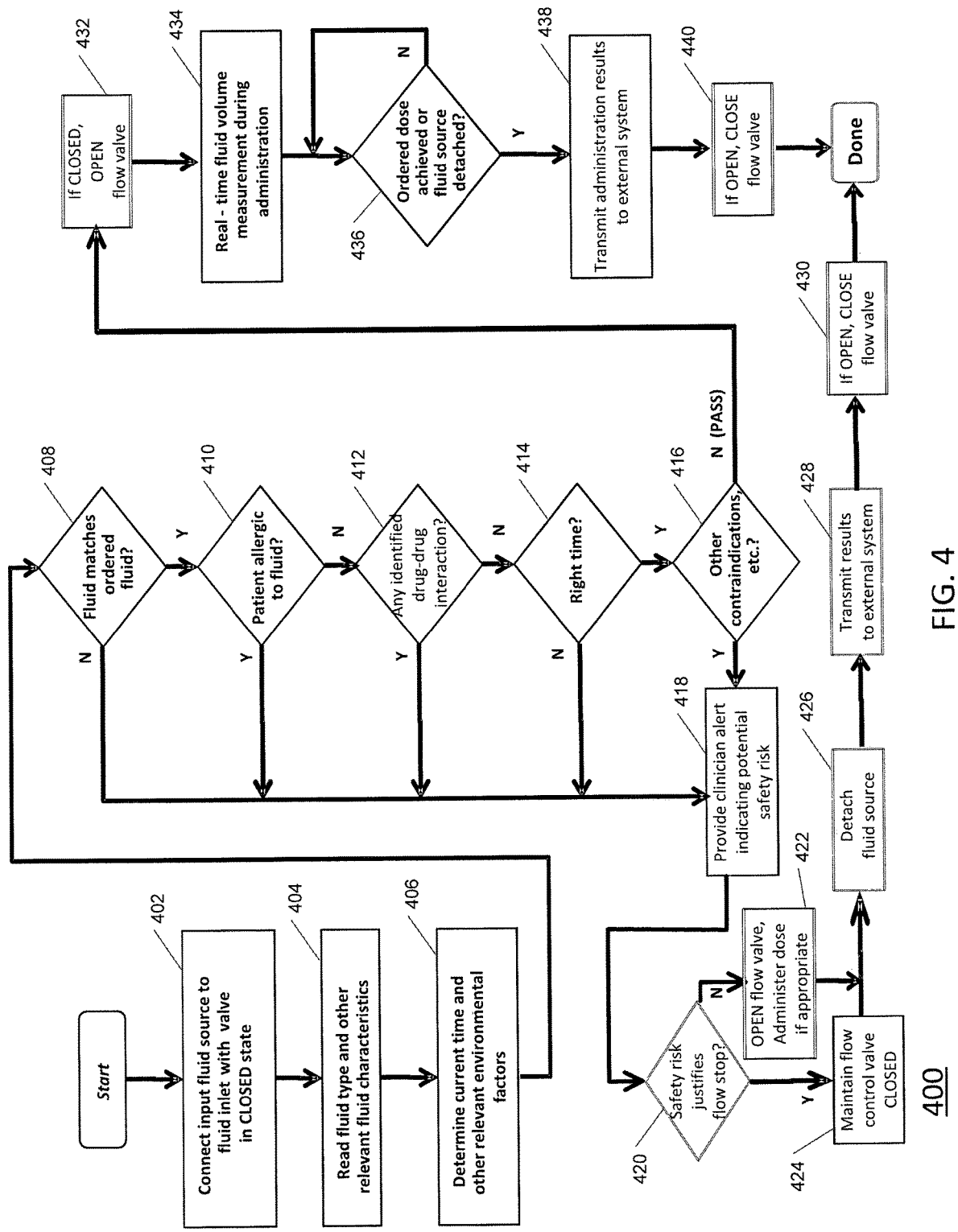
FIG. 4 is a flow chart illustrating an implementation of an operating mode of a system for controlling flow in a fluid delivery pathway.

As shown in the process flow diagram 400 of FIG. 4, the normally CLOSED mode is characterized by the flow control valve 115 normally in a closed state and temporarily opened to allow a fluid to pass through the fluid flow pathway 120. A fluid source can be connected with fluid inlet 105 while the valve 115 is in a closed state (402). Various relevant characteristics of the fluid source can be identified by the system 100 (404). The current time and other environmental factors can be determined (406). A series of safety checks can be performed by the flow-control software application to assess, for example, whether the fluid coupled to the inlet 105 matches a current medical order to deliver that fluid to the patient (408), the patient is allergic to the fluid connected to the fluid inlet 105 (410), whether any drug-drug interactions exist (412), whether the current time is the correct time for the administration of the attached fluid (414), or whether any other contraindications to administering the fluid to the patient exist (416). If the system 100 fails one or more of the safety checks, a determination can be made whether the safety risk justifies flow stop (420). If the risk does not justify the flow stop, then the flow valve can be opened and the caregiver can administer the dose (422), otherwise the flow control valve 115 is maintained in a closed position (424) by sending, for example, a flow state command 122 indicating that valve 115 should remain closed. Thereafter, the fluid source can be detached (426), results can be transmitted (428) to an external system 135, and if the valve is opened, the valve can be closed (430). In addition, the safety check can trigger an alert or warning to the clinician (418). Information associated with a resultant alert or warning (e.g. potential safety risk) can also be transmitted to an external system 135. If the system 100 passes all the safety checks, a flow state command 122 can be sent to the flow control valve 115 to open and allow fluid delivery to the patient.

If the system 100 does not fail one or more of the safety checks, the flow control valve 115, if closed, can be changed from a closed state to an open state (432). In some implementations, the system 100 can measure fluid volume in real-time during delivery of the fluid (434) and calculate the actual dose delivered and compare it to the ordered dose (436). The ordered "dose" can include a specific fluid volume (e.g. 1 liter of blood) or a quantity calculated by multiplying fluid volume by a fluid source concentration (e.g. 2 mL of 1 mg/mL concentration of morphine fluid source). Once the ordered dose is reached, the system 100 detects the fluid source is detached from the system 100, or fluid flow has stopped for a period long enough that the fluid flow controller can consider the dose administration to be complete, a flow state command 122 can be sent to close flow control valve 115 (440) in preparation for the next fluid administration. The administration conditions and results can be communicated to the system memory 150 and/or an external system 135 for recording (438).

In some implementations, the rules engine 130 logic can be defined such that triggering an alert or warning message to alert the clinician is an independent event from sending a flow state command 122 to flow control valve 115. Rules logic can generate tiered messages and/or flow state commands 122 using multiple trigger thresholds based on the severity of a potential safety risk. For example, if the physician-ordered dose for a fluid is 100 mL, the rules engine 130 can send a warning message to the clinician without closing the flow control valve 115 when the dose administered reaches 105 mL of fluid. However, if dose administration continues and the cumulative dose volume reaches 110 mL of fluid, the rules engine can send an alert message to the clinician while simultaneously sending a flow state command 122 to close flow control valve 115. The rules engine can poll remote data stores to obtain rules and/or flow control input data. This polling process may involve directly or indirectly utilizing subelements of flow control input data as reference parameters for accessing relevant external data. Such flow control input data can include, but not limited to, patient identifier information.

Figure 5:
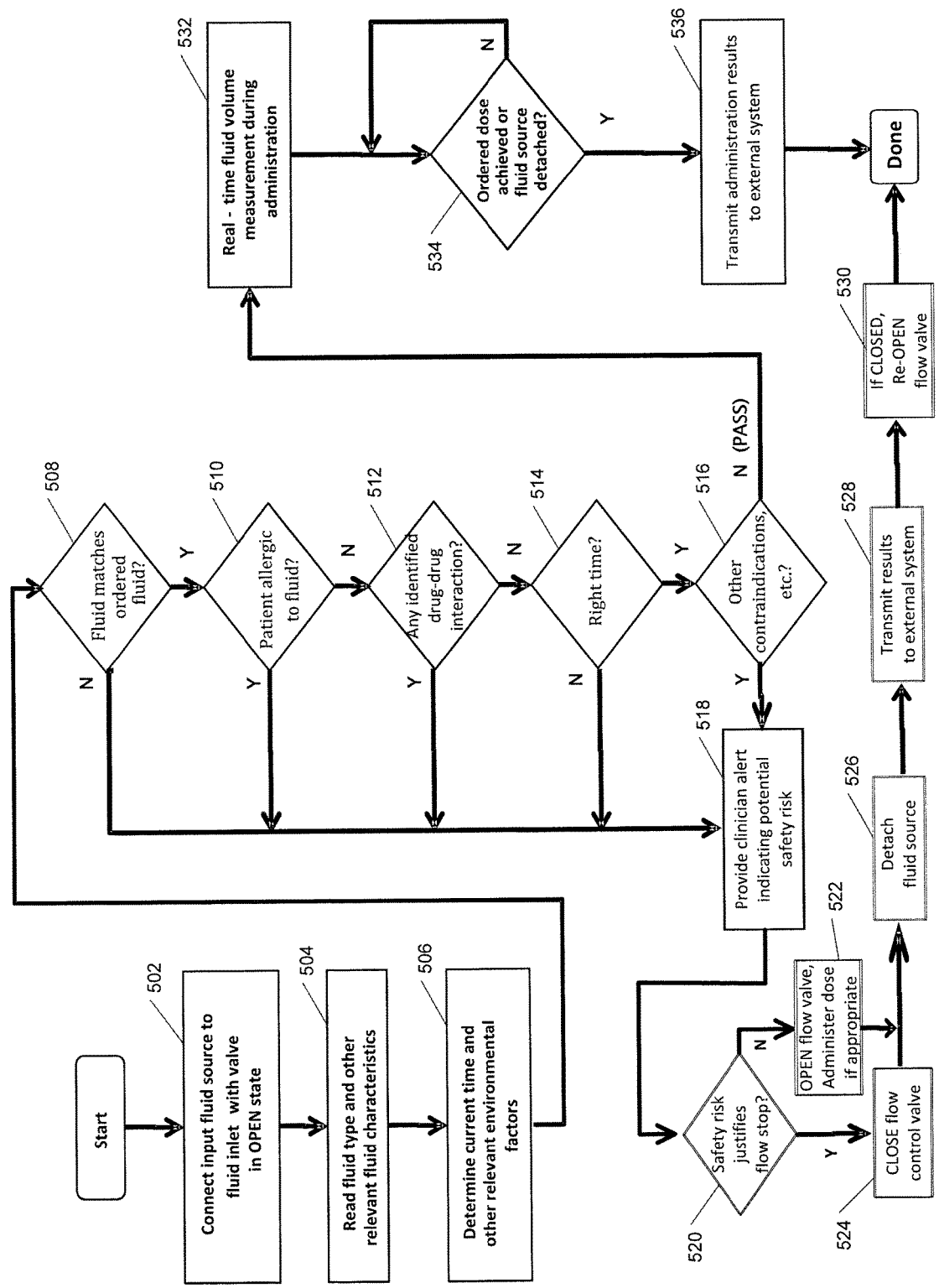
FIG. 5 is a flow chart illustrating another implementation of an operating mode of a system for controlling flow in a fluid delivery pathway.

Referring now to the process flow diagram 500 of FIG. 5, the normally OPEN mode is characterized by the flow control valve 115 normally in an open position to allow fluid to pass through the fluid flow pathway 120. A fluid source can be connected with a fluid inlet 105 while the flow control valve 115 is in the open state (502). Various relevant characteristics of the fluid source can be identified by the system 100 (504) as well as current time and environmental factors (506). A series of safety checks (508-516) similar to those described in connection with FIG. 4 can be performed by the flow controller software application using current flow control input data 140 as described above with respect to FIGS. 3-4. If one or more of the safety checks fail, an alert can be sent to the clinician (518), and if the safety risk justifies preventing fluid flow to the patient (520), then a flow state command 122 can be sent to close the flow control valve 115 (524). The fluid source can then be detached (526), results can be transmitted to an external system 135 (528), and the state of flow control valve 115 can be switched back to an open position (530). If one or more safety checks identify a potential risk but the risk does not justify closing flow control valve 115, then the fluid can be administered (522), the syringe can be detached (526), and the results can be transmitted to external system 135.

If no safety checks are triggered, fluid volume can be measured in real-time during administration (532). Once it is determined that the ordered dose has been achieved, the fluid source is detached, or fluid flow has stopped for a period long enough that the fluid flow controller can consider the dose administration to be complete (534), then results can be transmitted to external system 135 (536).

As described above, the rules engine can also trigger messages independent of flow state command 122 which can include transmitting data to record the condition in memory 150 of system 100 and/or to one or more external systems 135. Such triggers can also drive inputs and outputs on user interface 160. For example, outputs to the user through user interface 160 can include audio feedback, changes to status indicators, fluid source information, fluid composition information, volume of fluid administered, information associated with the fluid (e.g. medication) administration, rules engine information and/or output, error messages, feedback on the state of the flow control valve, or other similar parameters. Similarly, inputs from the user can include, but are not limited to, confirming an action, confirming recognition of an alert, entry of a manual override request for the flow control valve, or a reset of the valve.

While the set and sequence of safety checks utilized in FIGS. 4-5 illustrate one implementation of how elements of flow control input data 140 can be used by the system 100 flow controller to determine appropriateness of delivering a fluid to a patient, other implementations can include any mix and/or subset of flow control input data 140, with such data elements being operated on in any sequence of decision logic steps. In addition, although the decision logic represented in FIGS. 4-5 can be based on a linear sequence of simple binary decision checks, further implementations can include complex algorithms involving simultaneous consideration of multiple data elements and/or probability-based decision logic with fixed or configurable thresholds used to determine the proper flow state command 122 to send to flow control valve 115.

Figure 6:
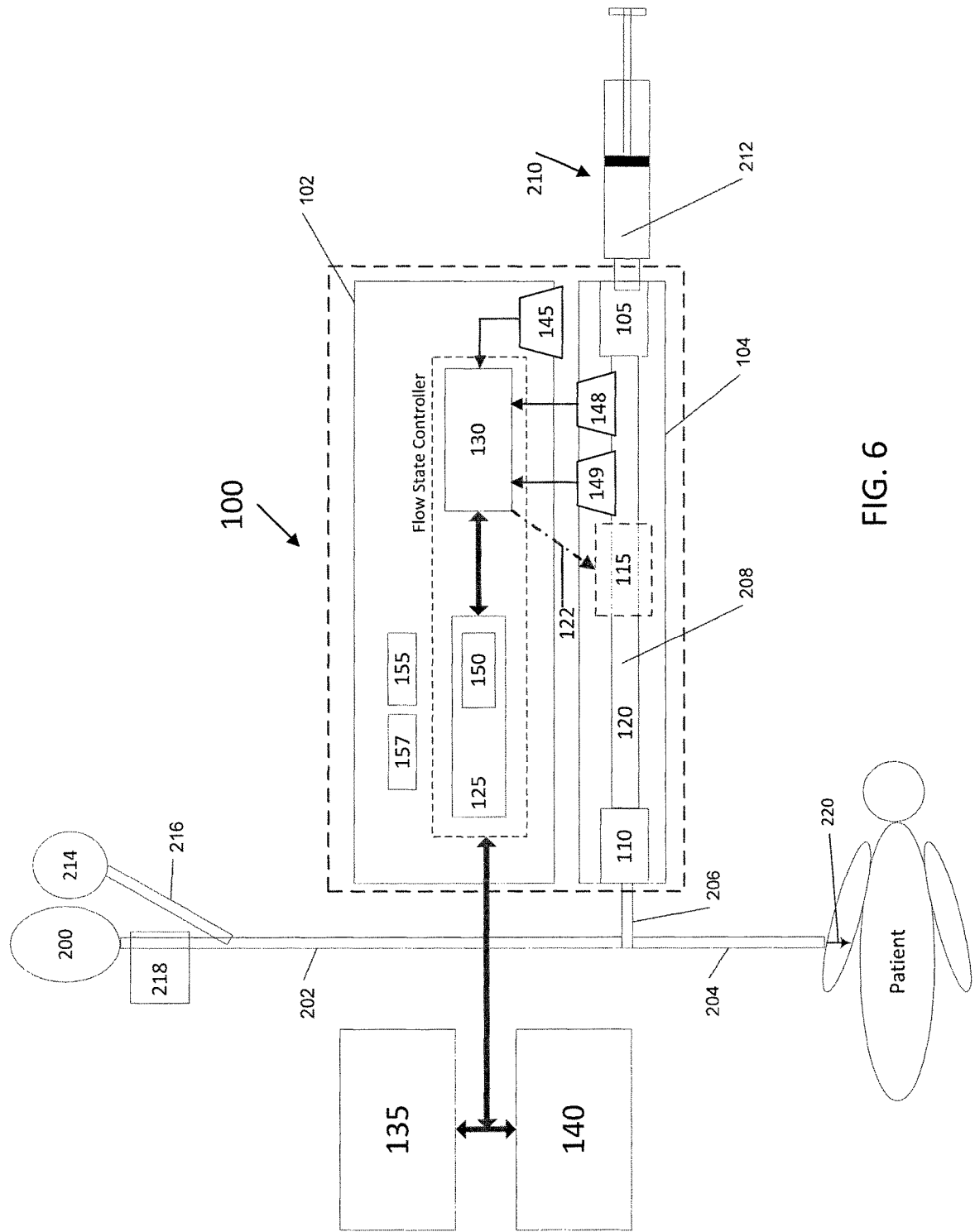
FIG. 6 is a diagram illustrating one configuration of fluid delivery tubing connected to a patient.

FIG. 6 is a diagram showing various illustrative arrangements of fluid delivery tubing 202, 204, 206 and 216 connected to a patient for the delivery of appropriate fluids. Primary fluid source 200 can be connected through tubing segment 202 and tubing segment 204 to a patient. Segment 204 can be attached to a patient by access device 220 such as a catheter or needle. Additionally, tubing segment 206 can be joined to upstream segment 202 and downstream segment 204 in between fluid source 200 and the patient. System 100 can be attached to segment 206 for the delivery of manually administered fluids. Fluid source 210, for example, can be a manually injectable syringe. Fluid 212 contained within fluid source 210 can be injected through fluid flow path 120, into segment 206, into segment 204 and finally through patient access device 220 and thereby administered to a patient. A fluid delivery pump 218 can be connected to segment 202 for continuous infusion of fluid. A secondary fluid source 214 can be connected to tubing segment 216. Tubing segment 216 can be joined with segment 202 for delivery of intermittent secondary fluids. System 100 can be separated into reusable subsection 102 and disposable subsection 104. Flow control valve 115 is shown within the disposable subsection 104.

In certain variations, certain elements of system 100 can be referred to as a housed and self contained fluid port 100. The elements of fluid port 100 minimally include fluid inlet 105, fluid flow pathway 120, at least one sensor (fluid identification sensor 145, and/or composition sensor 148, and/or fluid flow sensor 149), and wireless transmission electronics 157 that interface and/or communicate with the sensor 145 and/or 148 and/or 149 and communicate with systems that are external to the fluid port 100 in order to enable the actuation of a flow control valve 115. Fluid flow control valve 115 can be external to fluid port 100 as illustrated in FIG. 7. Certain portions of a flow controller that can include microprocessor 125, memory 150, and rules engine 130 can also be contained in fluid port 100. Thus in certain variations a self-contained fluid port 100 can include some or all of the elements depicted for system 100. Fluid port 100 can serve as a compact, self-contained port for manual injection of medications and other fluids into fluid inlet 105 and then into tubing segment 204 that leads to patient access device 220. Fluid port 100 can be small and light enough to enable fluid port 100 to be suspended from tubing 202. Fluid port 100 can include a reusable subsection 102 and a disposable subsection 104. A compact housing (combination of 102 and 104) can contain all the elements of port 100.

FIG. 6 illustrates the use of three discrete sensor types: fluid identification sensor 145, fluid composition sensor 148, and fluid flow sensor 149. Variations can include a single sensor type or a mix of sensors. In variations involving multiple sensors, the sensors can be used independently or in tandem to provide input to rules engine 130. In one example, a system 100 can include only a composition sensor 148 that, following the start of fluid delivery from a manually administrable fluid source, enables the flow controller to determine the nature of flow state command 122 based on confirmation that the types and relative concentrations of fluid constituents sensed by composition sensor 148 are appropriate for administration to a patient. Composition sensor 148 can incorporate a variety of technologies, including but not limited to, photometric analysis, electrometric analysis, chromatography, mass spectroscopy, physical property measurements, or it can utilize a parametric analysis based on a combination such technologies. In another example, a system 100 can include an identification sensor 145 and fluid flow sensor 149, where the identification sensor 145 is used to confirm a correct fluid type for the patient and fluid flow sensor 149 is used to determine when flow control valve 115 should be closed based on a prescribed fluid dosage. Fluid flow sensor 149 can be based on technologies, including but not limited to: a paddle wheel flow meter, a turbine flow meter, a thermal flow meter, a pressure sensor, a differential pressure sensor, an optical sensor, an ultrasonic sensor, a coriolis flow meter, a displacement sensor.

It should be appreciated that the use of multiple sensor types, used separately or in parallel, are fully applicable to the various fluid delivery set configurations described in FIGS. 2A-2G. Furthermore, the flow control valves 115 illustrated in the FIGS. 2A-2G can be integrated within the fluid sets, external to the sets while still existing as subcomponents of system 100, or independent of, but in communication with system 100. In FIG. 2B, for example, the "Y-site" inlets 205a and 205b can each contain identification sensors 145, that when used to identify the fluid coupling of an inappropriate fluid source to either inlet, can enable the flow controller to communication with an external system containing a flow control valve 115 to initiate a flow rate change or shutdown of fluid flow in the pathway leading to the patient. In some implementations, flow control valve 115 can communicate (e.g. via wireless transmitter associated with the valve) changes in valve status to the flow controller to provide feedback in response to having received a flow state command 122.

FIG. 7 is a diagram illustrating a physically separated flow control valve 115 in various positions on the fluid delivery tubing. The flow control valves 115 in this system may be in one or more of the illustrated (dashed) locations with respect to this fluid delivery arrangement. In this variation, flow control valve 115 can be physically separated from system 100. The flow control valve 115 can be located upstream (positions 230 and 240) or downstream (position 250) of segment 206 and fluid port 100. The flow control valve 115 can be within an external device 218 like an infusion pump (position 230). Alternatively, flow control valve 115 can be below a "Y" site (position 240) and control both primary fluid source 200 and secondary source 214. Alternatively, flow control valve 115 can be positioned close to the patient (position 250) and control primary fluid source 200, secondary fluid source 214 and fluid source 210 (a syringe for injection into inlet 105). Alternatively, flow control valve 115 can be within system 100 as discussed in FIG. 6 connected between tubing segment 206 and fluid source 210.

Figure 8:
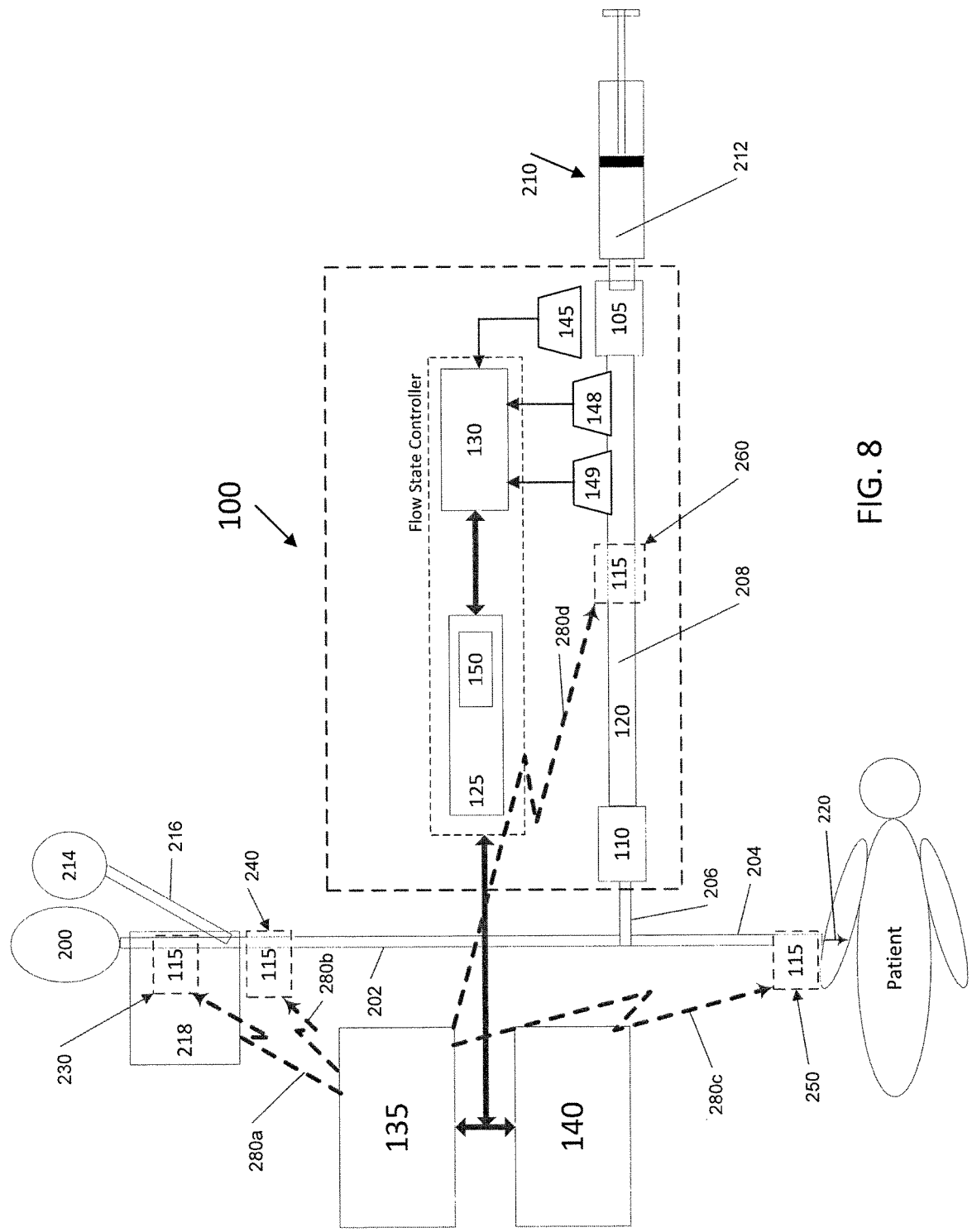
FIG. 8 is a diagram illustrating various alternatives for origination of a flow control command.

FIG. 8 is a diagram illustrating various alternatives for the origination of a flow control command 122 from external devices/systems 135. A flow controller and/or a rules engine 130 can be included to determine the appropriate state of the flow control valve 115 (open or closed). The flow controller and/or the rules engine 130 can be external to the system and/or be distributed across several system elements. If distributed, the logic could cascade across systems (e.g.: IF an outside rule is met AND an inside rule is met, THEN a trigger flow control command 280 can be activated). The flow control valve 115 can be responsive to a command 280 from the flow controller and/or rules engine 130 based on information provided by the fluid identification sensor 145 and/or a fluid composition sensor 148, and/or flow sensor 149. The flow control valve 115 can be wirelessly connected or wired to the external system 135, flow controller and/or rules engine 130. One alternative can include flow state command 280a controlling flow valve 115 in position 230. A second alternative can include flow state command 280b controlling fluid flow control valve 115 in position 240. A third alternative can include flow state command 280c controlling flow control valve 115 in position 250. A fourth alternative can include flow state command 280d controlling flow valve 115 in position 260. A fifth alternative can include flow state command 280 (commands 280a, 280b, 280c, or 280d not shown) originating from microprocessor 125. Other alternatives can be envisioned for positioning fluid flow control valve 115 in various flow path segments and controlled by various flow controller commands 280.

In some variations, flow control valve 115 can control the flow rate in a binary manner (open or closed) or in other variations it can partially restrict flow and thus limit the flow rate to a specific flow rate level. The flow control valve 115 can be powered by a self-contained power source or connected to an external power source. The flow control valve 115 can be a one-time activated device or can be resettable enabling repeat activation. The flow controller command signal 280 can be published as an open-source such that any appropriate system or device could send command 280 and activate flow control valve 115.

Figure 9:
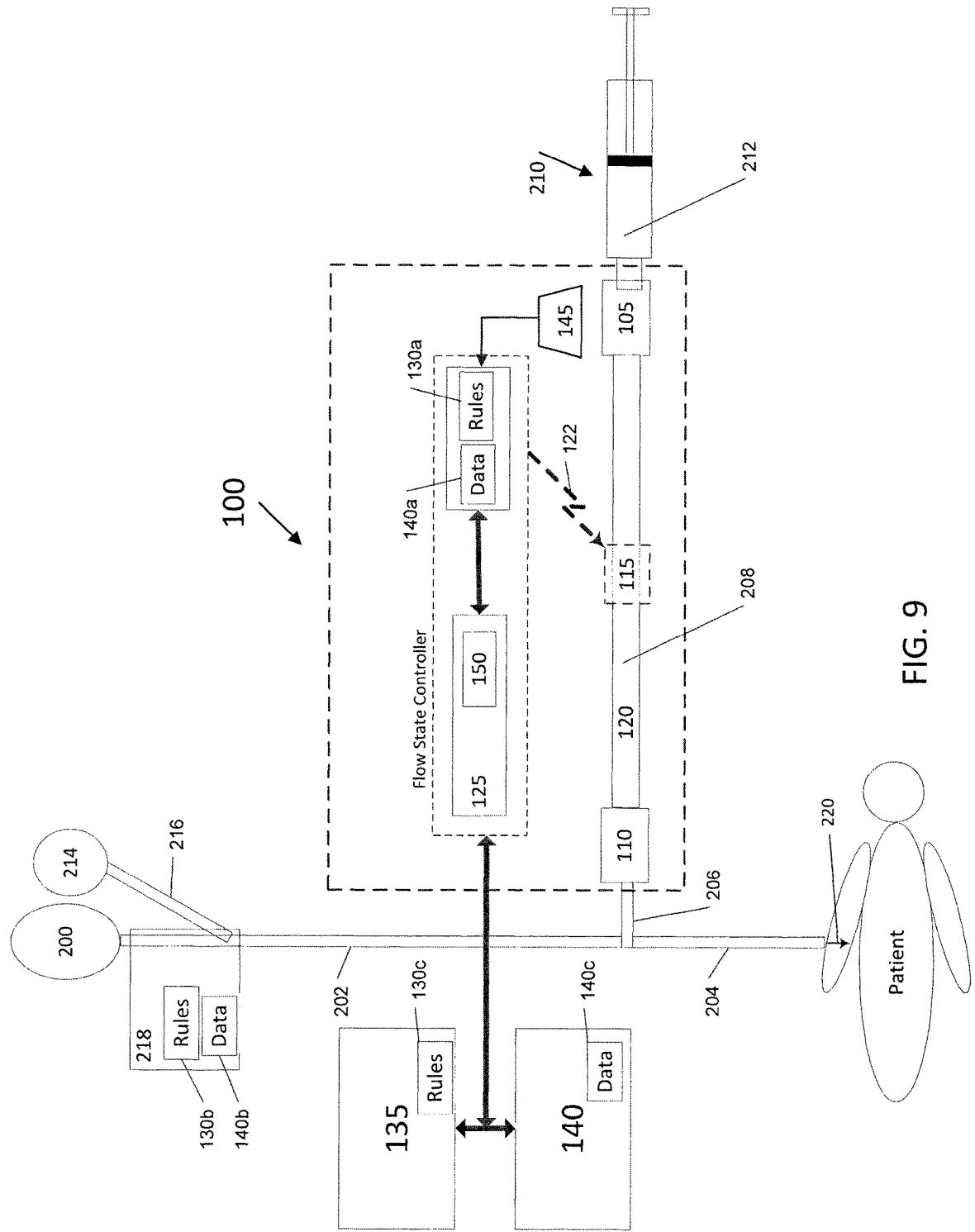
FIG. 9 is a diagram illustrating various alternative locations of rules and data.

FIG. 9 is a diagram illustrating various alternative locations of rules and data. Rules engine 130 (130a, 130b, 130c) can reside at various locations and/or be distributed having some rules inside system 100 and some rules outside system 100. In one alternative, rules engine 130a can be inside system 100. In another alternative, rules engine 130b can be inside an external device (infusion pump) 218. In another alternative, rules engine 130c can be inside external system 135. If distributed, the rules logic can cascade across systems and activate flow control valve 115. Similarly, flow control data 140 (140a, 140b, 140c) can be distributed across systems. In one alternative, flow control data 140a can be in the flow controller. In a second alternative, flow control data 140b can be in the external device (infusion pump) 218. In a third alternative, flow control data 140c can be in external flow control data source 140.

Figure 10:
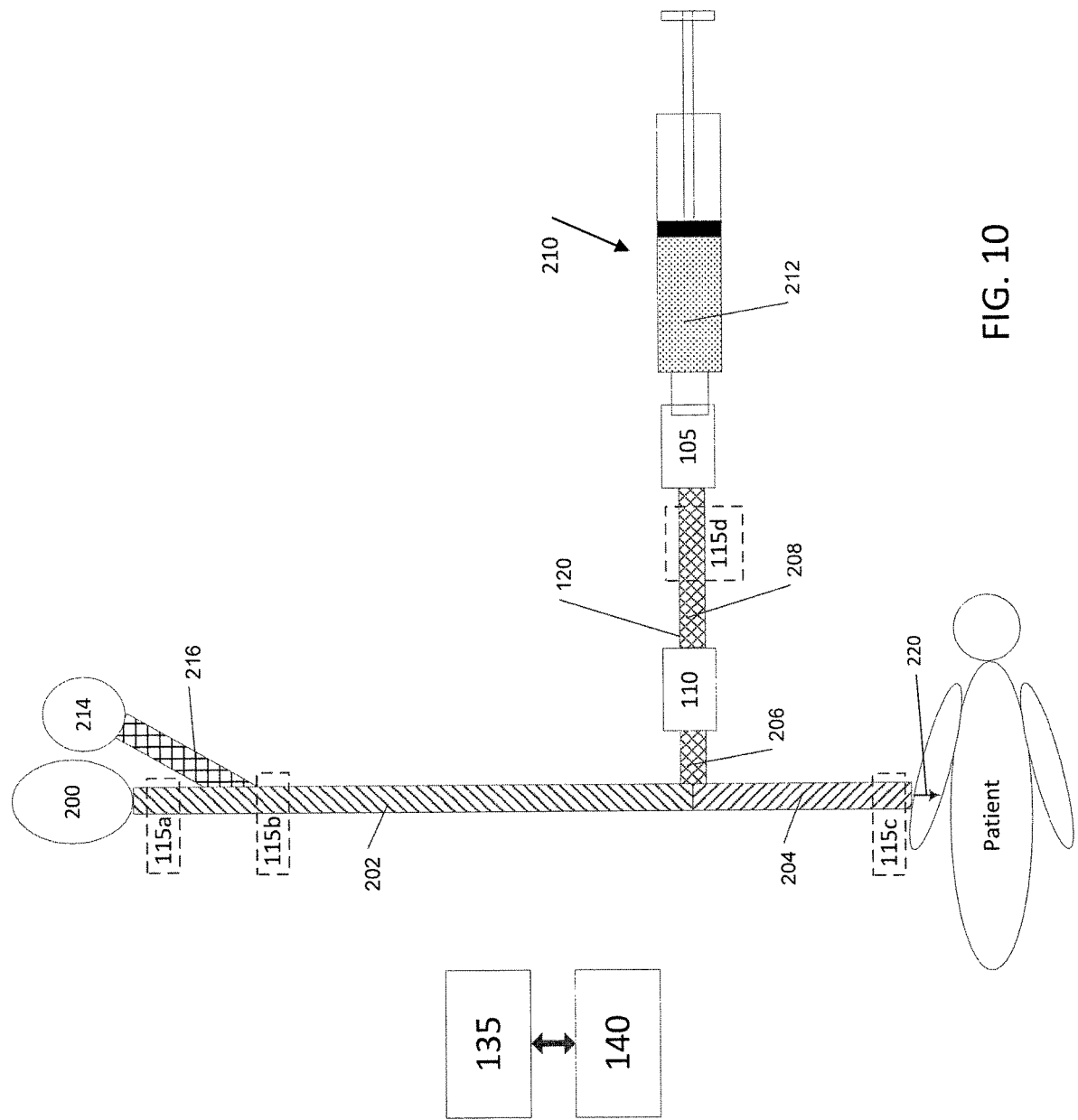
FIG. 10 is an illustration of various volume and flow rate components of the fluid delivery pathway.

FIG. 10 is an illustration of various volume and tubing components of the fluid delivery pathway. The tubing system can include flow paths with known volumes and flow rates. Primary tubing segment 202 has a known volume V1 and a flow rate R1, side tubing segment 206 volume plus fluid flow pathway 120 (volume 208) has a known volume of V2 and a flow rate R2 (speed of injection using syringe 210) and lower tubing segment 204 has a known volume V3 and a flow rate R3 (sum of R1 plus R2). When a known volume of fluid 212 is injected into a flowing fluid pathway 202/204 the time T1 for the injected fluid to reach the patient can be calculated. Flow control valve 115 (115a, 115b, 115c or 115d) can be activated before an inappropriate fluid 212 can reach the patient. A safety confirmation of fluid stop can be provided to the patient caregivers by user interface 160.

An example of the time calculations follows:
 tubing segment 202 could contain V1=10 mL of fluid volume and be flowing at a rate of R1=60 mL/hour.
 tubing segment 206 plus tubing segment 208 (fluid flow pathway 120) is typically small and could contain V2=1 mL of fluid volume.
 tubing segment 204 is moderately sized and could contain V3=3 mL of fluid volume flowing at a rate R3=R1 prior to and after injection of fluid volume 212 and R1+R2 during injection of volume 212.
 fluid injection volume 212=V4=3 mL of fluid volume and is injected at a rate of 3 mL/3 sec=R2=1 mL/sec.=60 mL/min.
 flow rate R3 will return to =R1 when syringe 210 has been fully injected.
 Therefore, calculating the time $t_x=t_1+t_2$ for injection fluid 212 to reach the patient:
 where $t_1$=time for injection volume to get into the primary tubing segment 202
  $t_1$=Volume/Rate=(V2+V3)/R2=(1 mL+3 mL)/60 mL/min=4 mL/60 mL/min
  $t_1$=1/15 minutes=4 seconds
 where $t_2$=time for injection volume 212 to flow into the patient thru segment 204
  $t_2$=V3/R1=3 mL/(60 mL/hour)=3 mL/1 mL/min=3 minutes
 time $t_x=t_1+t_2$=4 seconds+3 minutes=184 seconds for all of fluid 212 to reach the patient.

It should be noted that some of the fluid reaches the patient earlier and that the response time for flow control valve 115 is important to limit patient exposure to inappropriate fluid administration. Positioning of flow control valve 115 near the patient is thus important. Additionally, early detection of an inappropriate fluid is also important to protect the patient. Operation of identification sensor 145 to detect fluid source 210 at the time of attachment to fluid inlet 105, before manual administration fluid flow, is preferred. Alternatively, composition sensor 148 can identify fluid 212 and/or flow sensor 149 can measure fluid volume 212 providing data for the flow controller.

Additionally, fluid volume V2+V3 downstream from the injection port can be measured by fluid withdrawal into a syringe 210 (pulling on an empty syringe connected to the injection port and withdrawing fluid into the syringe) with the upstream fluid pathway 202 occluded (pinched off). The withdrawn downstream fluid volume V2+V3 can be measured manually by inspection of the syringe graduations or measured automatically by a fluid volume measurement sensor 149 within the injection port apparatus (if so enabled to detect reversed flow). The measured downstream volume can be communicated to and stored in the rules engine. The downstream volume can then be used as an input to the flow controller.

In yet another variation, flow control valve 115 can be distributed between a disposable subsection and a reusable subsection. The interface between these subsections can be electrical, magnetic, mechanical, hydraulic, optical, and/or capacitive. The disposable subsection can include the flow control valve 115 and fluid flow pathway 120 only and the reusable subsection can include all the other operational components. In this configuration the valve actuator is in the reusable subsection coupled to the disposable subsection valve 115 mechanism with fluid flow pathway 120. Alternatively, the disposable subsection can include all the components including the flow control valve 115, power supply, wireless or wired communications, and fluid path.

It should be appreciated that the systems described herein can, but need not transmit data to an external system 135 for recording and logging data. For example, the system 100 can incorporate the intelligent flow control features of the programmable flow control valve 115 and provide user feedback (such as alarms and other alert messages to user interface 160) without transmitting, and/or recording the data to an external system 135.

The system 100 can be programmed with information downloaded into the system memory 150 prior to use, in real-time, using on-demand connectivity with the external systems 135 or a combination of the two. In some implementations, the system 100 can be pre-programmed according to a subset of static flow control data 140 (e.g. patient blood type, known drug allergies, dose limits, etc.) prior to or upon connection to a patient's fluid line. The system 100 can be programmed using a dockable cradle, wireless communications interface or a wired connector. In some implementations, a low-cost, non-wireless version of the system 100 can be pre-programmed with only non-patient-specific rules such as drug-drug interactions, hard dosing limits, etc. for generic use with any patient. The system 100 can be provided to a buyer including the pre-programmed with non-patient-specific information or according to published clinical guidelines and standards. The non-patient-specific information can be programmed prior to clinical use by a manufacturer, care provider or by a hospital pharmacist, or other care setting based on provider-specific rules and operating procedures.

In some implementations, the system 100 can be programmed and/or communicate information in real-time to the one or more external systems 135 using a wireless transmission 157. A variety of wireless transmission hardware and protocols can be used such as RF, IrDA (infrared), Bluetooth, Zigbee, Continue, Wireless USB, Wibree, IEEE 802 relevant standards (e.g., 802.11, 802.15, or 802.16, etc.), Direct Sequence Spread Spectrum; Frequency Hopping Spread Spectrum; cellular/wireless/cordless telecommunication protocols, wireless home network communication protocols, paging network protocols, magnetic induction, satellite data communication protocols, wireless hospital or health care facility network protocols, and other methods. The data transmissions can, in some implementations, be encrypted in order to ensure patient privacy and/or to comply with various laws relating to handling of medical data. The transmitter can have such encryption capabilities or one or more additional chipsets can be incorporated within a region of the system 100 to provide such encryption.

In some implementations, the configurable rules engine 130 can run on a microprocessor 125 remote to the system 100. The flow state commands 122 or 280 can be sent to the system 100 in a wireless or wired manner to the flow control valve 115 instructing the flow control valve 115 to open or close.

The system 100 described herein can include one or more mechanisms configured for receiving input from a user via user interface 160 to control operation of the system 100 and/or providing feedback to a user from the system 100. For example, the user interface 160 can incorporate one or more user inputs such as one or more keys, buttons, switches, dials, or touch-screens. The user interface 160 can incorporate one or more user feedback mechanisms such as one or more LEDs, graphical displays, sounds, speech synthesis technology or vibration mechanisms. The visual, tactile or auditory feedback can include a sequence of notifications such as volume, color, number, intensity, or other feature of the particular feedback mechanism is varied to indicate a particular state of the system 100. Information provided by a user via user interface 160 can be used by the flow controller in determining an appropriate flow state command 122 to flow control valve 115. In some implementations, one or more of the user inputs and/or feedback mechanisms of user interface 160 can be remote to the system 100, such as on a computing device in communication with the system 100 such as by a wired or wireless connection using the transmitter/receiver 157.

The power source 155 can include a self-contained power source such as a battery, single-use or rechargeable battery, battery array or other type of power source known in the art. Where the battery is rechargeable, there can be a connector or other interface for attaching the device to an electrical outlet, docking station, portable recharger, or so forth to recharge the battery.

In some implementations, the system 100 can include an internal fluid composition sensor 148 that can be configured to allow the fluid composition and concentration of the fluid source to be empirically determined. The sensor 148 can be positioned downstream of the fluid inlet 105 and upstream of flow control valve 115. The internal fluid composition sensor 148 can be the sole source of fluid type detection. In some implementations, the composition sensor 148 can be a supplement to fluid source information carried by the fluid source container and detected by a fluid source reader 145.

The system 100 can accommodate a variety of volumes and doses, including fractional doses, or multiple fluid source connections to fulfill the desired treatment protocol of a single patient medical order. For example, a physician can order a 2 mg dose of morphine for a patient. The nurse can connect one 4 mg syringe of morphine, intending to deliver half the syringe to the patient and discard the other half. In this example, the system 100 can alert the clinician that a 4 mg syringe is connected to the system 100 and the potential dose to be delivered to the patient is too high. The system 100 can also prevent overdose by sending a flow state command 122 or 280 to close the flow control valve 115 after the first 2 mg of morphine have been delivered to the patient to prevent delivery of remaining 2 mg of morphine. Alternatively, a physician can order 2 mg of morphine for a patient. The care provider can fulfill the order by first connecting a 1 mg syringe of morphine to the system 100 and delivering the full contents of the syringe to the patient and then connecting a second 1 mg syringe of morphine to the system 100 and delivering the full contents of the second syringe to the patient. In either scenario, the physician order for 2 mg have been fulfilled and the system 100 would not provide an alert or constrain fluid flow unless a further morphine syringe is coupled to the system 100.

In some cases, different flow restriction mechanisms can be used other than a flow control valve. In such cases an operation modification signal can be generated (based on attributes detected by the sensor(s) as applied to various rules) which causes one or more devices to change an operational parameter which directly or indirectly affects fluid flow within the fluid pathway(s) (at various points along the fluid pathway(s)). In other variations, a fluid port can generate an operation modification signal (based on attributes detected by the sensor(s) as applied to various rules) which causes other operational parameters of an external device to change. Such operational parameters need not necessarily affect fluid flow through the fluid pathway(s).

Similarly, the systems described herein can use any sort of manually administered fluid source and are not limited to a specific IV fluid source type and can include syringes, IV bags, disposable medication cartridges or pouches, IV tubing, etc.

It should be appreciated that the systems described herein can be used for delivery of fluids by a variety of routes of administrations. Unless otherwise specified the terms injection, administration, or delivery as they relate to introducing a fluid to a patient is not intended to be limiting to a particular route of manual administration (i.e., administration effected by a human being as opposed to a pump).

Various aspects of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communications network). Examples of communications networks include a local area network ("LAN"), a wide area network ("WAN"), and the Internet.

The computing system may include clients and servers. A client and server are generally remote from each other and typically interact through a communications network. The relationship of client and server arises by virtue of computer programs running on the respective computers and having a client-server relationship to each other.

The implementations set forth in the foregoing description do not represent all implementations consistent with the subject matter described herein. Instead, they are merely some examples consistent with aspects related to the described subject matter. Wherever possible, the same reference numbers will be used throughout the drawings to refer to the same or like parts.

Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows and steps for use described herein do not require the particular order shown, or sequential order, to achieve desirable results. Other embodiments can be within the scope of the claim.

What is claimed is:

1. A system comprising:
    a fluid port comprising:
        a fluid channel;
        a fluid inlet at a first end of the fluid channel configured to couple to an outlet of a manually administrable fluid source;
        a fluid outlet at a second end of the fluid channel configured to deliver fluid from the manually administrable fluid source to a fluid pathway that provides the fluid to a patient;
    at least one sensor configured to determine at least one attribute of the fluid from the manually administrable fluid source;
    a flow controller in communication with the at least one sensor that generates at least one flow modification signal in response to the determined at least one attribute matching at least one condition specified by at least one rule; and
    a flow control valve in communication with the flow controller, the flow control valve changing a level of flow restriction of the fluid from the manually administrable fluid source passing therethrough in response to receiving the at least one flow modification signal,
    wherein the at least one sensor is configured to automatically measure a withdrawn downstream fluid volume, wherein the withdrawn downstream fluid volume is a total volume of the fluid downstream of the fluid inlet and still within the fluid channel after fluid flow through the fluid pathway is stopped, and
    wherein the at least one sensor comprises a fluid flow sensor, and wherein sensed fluid flow information causes the flow controller to generate a first flow modification signal to cause the flow control valve to transition to a first state when a first pre-determined volume has been delivered as measured by the fluid flow sensor, and after a pre-determined span of time, causes the flow controller to generate a second flow modification signal to cause the flow control valve to transition to a second state different than the first state.

2. The system as in claim 1, wherein the flow control valve is positioned at a location that is physically separated from the fluid port.

3. The system as in claim 2, wherein the flow control valve is positioned upstream from the fluid port.

4. The system as in claim 2, wherein the flow control valve is positioned downstream from the fluid port.

5. The system as in claim 2, wherein the flow control valve is positioned at the location to control flow of multiple fluids including the fluid to the patient.

6. The system as in claim 1, wherein the flow control valve is positioned inline between the fluid inlet at the first end of the fluid channel and the fluid outlet at the second end of the fluid channel.

7. The system as in claim 1, wherein changing the level of flow restriction of the fluid from the manually administrable fluid source passing through the flow control valve comprises adjusting a current flow rate of the fluid passing through the flow control valve to a higher or lower flow rate, wherein the flow control valve partially restricts the fluid passing through the flow control valve at the higher or lower rate.

8. The system as in claim 1, wherein the at least one sensor determines the at least one attribute of the fluid from the manually administrable fluid source when the manually administrable fluid source is being coupled to the fluid inlet, when the manually administrable fluid source is coupled to the fluid inlet, and/or when the fluid is passing through the fluid channel.

9. The system as in claim 1, wherein changing the level of flow restriction of the fluid from the manually administrable fluid source passing through the flow control valve comprises stopping all of the fluid from passing through the flow control valve.

10. The system as in claim 1, wherein the flow controller comprises or is in communication with a rules engine, the rules engine using a plurality of rules to determine whether the at least one attribute matches the at least one condition specified by the at least one rule.

11. The system as in claim 10, wherein the flow controller polls at least one remote data source to obtain at least a portion of the plurality of rules.

12. The system as in claim 10, wherein the rules engine, when applying the plurality of rules, uses (i) the at least one attribute and (ii) flow control input data selected from a group consisting of: fluid information, patient-specific information, medical order information, clinical guideline information, environmental factors, flow control valve status, and historical information.

13. The system as in claim 1, wherein the outlet of the manually administrable fluid source comprises fluid source information encoded thereon, and the at least one sensor comprises an identification sensor that detects the manually administrable fluid source information when the manually administrable fluid source is being coupled or is coupled to the fluid port inlet.

14. The system as in claim 13, wherein the fluid source information is a code or identifier used to reference a secondary data set that is associated with the fluid contained within the manually administrable fluid source.

15. The system as in claim 14, further comprising a memory that stores the secondary data set and a remote data source coupled to the flow controller via a communications network that stores the secondary data set.

16. The system as in claim 13, wherein the at least one flow modification signal is generated using a rules engine that processes the detected manually administrable fluid source information.

17. The system as in claim 1, wherein the at least one sensor comprises a fluid composition sensor that determines a composition of the fluid, the fluid composition sensor is located along the fluid channel between the fluid inlet and the fluid outlet, and the at least one attribute is indicative of at least one constituent present in the fluid flowing through the fluid channel.

18. The system as in claim 17, wherein the at least one flow modification signal is generated using a rules engine that processes the result of the sensed fluid composition information.

19. The system as in claim 1, wherein contents from the manually administrable fluid source do not reach the patient for at least a time T1 after the manually administrable fluid source begins fluid delivery into the fluid inlet, the flow controller and the flow control valve are configured to restrict flow in the fluid pathway within a time T2<T1 after the manually administrable fluid source begins the fluid delivery into the fluid inlet.

20. The system as in claim 1, further comprising a wireless transmitter to transmit data from the at least one sensor to the flow controller.

21. The system as in claim 1, further comprising a wireless transceiver coupled to the flow controller to receive and transmit data relating to operation of the flow control valve and a wireless receiver coupled to the flow control valve to receive the at least one flow modification signal from the flow controller.

22. The system as in claim 21, further comprising a wireless transmitter coupled to the flow control valve to send information to the flow controller indicative of a change in the level of fluid flow restriction being applied to the fluid passing through the flow control valve in response to receiving the at least one flow modification signal from the flow controller.

23. The system as in claim 1, wherein the fluid port further comprises a wireless transceiver for transmitting and receiving data to and from the flow controller, and the flow controller further comprises a wireless transceiver for transmitting and receiving data to and from the fluid port.

24. The system as in claim 23, wherein the flow controller transmits data to an external device other than the fluid port controlling a state of the flow control valve.

25. The system as in claim 1, wherein the at least one flow modification signal is automatically initiated and executed by the flow controller without user intervention.

26. The system of claim 1, further comprising:
an interface to provide at least one of audio and visual feedback to a user associated with at least one of the at least one attribute and the fluid contained within the manually administrable fluid source.

27. The system as in claim 26, wherein the interface provides an indication to the user of the first state and the second state of the flow control valve.

28. The system as in claim 1 further comprising a manual override element, which when activated by a user, causes the flow controller to cause the flow control valve to stop fluid flow in the first state or to allow the fluid to flow in the second state.

29. The system of claim 1, further comprising a communications module to at least transmit or receive at least one of flow control input data, rules engine output data, and data on the manually administrable fluid source to or from a remote data processing system.

30. The system of claim 1, wherein there are a plurality of fluid inlets, each configured to couple to an outlet of one of a plurality of manually administrable fluid sources.

31. The system as in claim 30, wherein there are a plurality of flow control valves, each flow control valve being coupled to the flow controller to selectively prevent the fluid flowing from at least one of the plurality of fluid inlets.

32. The system as in claim 1, wherein the flow controller receives data relating to the patient that is used, in combination with information from the at least one sensor, to determine whether to generate the at least one flow modification signal.

33. The system as in claim 1, wherein the at least one sensor comprises a fluid flow sensor, and wherein the system further comprises:
an interface providing at least one of audio and visual feedback indicating how much of the fluid has been delivered as measured by the fluid flow sensor.

34. The system as in claim 1, wherein at least the fluid inlet, the fluid outlet, and the fluid channel are disposed within a disposable sub-housing and the disposable sub-housing is included in a sterile pouch enveloping the disposable sub-housing.

35. The system of claim 1 further comprising a housing enveloping at least a portion of each of the fluid inlet, the fluid outlet, the flow controller, and the at least one sensor.

36. The system as in claim 1, wherein the at least one sensor polls a remote data source or data processing system to generate the at least one attribute.

37. The system as in claim 1, wherein the flow controller polls at least one remote data source or data processing system to determine whether the at least one attribute matches the at least one condition specified by the at least one rule.

38. A system comprising:
a fluid port comprising:
a fluid channel;
a fluid inlet at a first end of the fluid channel configured to couple to an outlet of a manually administrable fluid source; and
a fluid outlet at a second end of the fluid channel configured to deliver fluid from the manually administrable fluid source to a fluid pathway that provides the fluid to a patient;
at least one sensor configured to determine at least one attribute of the fluid from the manually administrable fluid source;
a controller in communication with the at least one sensor that generates at least one operation modification signal in response to the determined at least one attribute matching at least one condition specified by at least one rule; and
a transmitter for wirelessly transmitting the at least one operation modification signal to at least one device, the at least one operation modification signal, when received by the at least one device, causing the at least one device to modify at least one operating parameter,
wherein the at least one sensor comprises a fluid flow sensor, and wherein sensed fluid flow information causes the controller to generate a first operation modification signal to cause a flow control valve to transition to a first state when a first pre-determined volume has been delivered as measured by the fluid flow sensor, and after a pre-determined span of time, causes the controller to generate a second operation modification signal to cause the flow control valve to transition to a second state different than the first state, wherein, the fluid pathway has a known volume and a known flow rate and the at least one sensor is configured to automatically measure a withdrawn downstream fluid volume, and wherein the withdrawn downstream fluid volume is a total volume of the fluid downstream of the fluid inlet and still within the fluid channel after fluid flow through the fluid pathway is stopped.

39. The system as in claim 38, wherein the controller also generates at least one operation modification signal based on the known volume and the known flow rate, wherein the controller determines a time for the injected fluid to reach the patient from the manually administrable fluid source based on the known volume and the known flow rate to generate the at least one operation modification signal.

40. A method comprising:
receiving data generated by at least one sensor of a fluid port including at least one attribute of fluid within a manually administrable fluid source, the fluid port comprising: a fluid channel, a fluid inlet at a first end of the fluid channel configured to couple to an outlet of the manually administrable fluid source, and a fluid outlet at a second end of the fluid channel configured to deliver the fluid from the manually administrable fluid source to a fluid pathway that provides the fluid to a patient, wherein the at least one sensor comprises a fluid flow sensor;
determining that the at least one attribute in the received data matches at least one condition specified by at least one rule;
generating at least one flow modification signal, which causes a change in the fluid passing through the fluid pathway;
receiving data generated by the at least one sensor of the fluid port including a withdrawn downstream fluid volume, wherein the withdrawn downstream fluid volume is a total volume of the fluid downstream of the fluid inlet and still within the fluid channel after fluid flow through the fluid pathway is stopped; and
generating, based on sensed fluid flow information from the fluid flow sensor, a first flow modification signal to cause a flow control valve to transition to a first state when a first pre-determined volume has been delivered as measured by the fluid flow sensor, and after a pre-determined span of time, generating a second flow modification signal to cause the flow control valve to transition to a second state different than the first state.

41. A method comprising:
receiving data generated by at least one sensor of a fluid port, the data including at least one attribute of fluid within a manually administrable fluid source, the fluid port comprising: a fluid channel, a fluid inlet at a first end of the fluid channel configured to couple to an outlet of the manually administrable fluid source, and a fluid outlet at a second end of the fluid channel configured to deliver the fluid from the manually administrable fluid source to a fluid pathway that provides the fluid to a patient wherein the at least one sensor comprises a fluid flow sensor;
determining that the at least one attribute in the received data matches at least one condition specified by at least one rule;
generating, by a controller in communication with the at least one sensor, at least one operation modification signal in response to the at least one attribute matching at least one condition specified by at least one rule; and
wireless transmitting, by a transmitter, the at least one operation modification signal to at least one device, the at least one operation modification signal, when received by the at least one device, causes the at least one device to modify at least one operating parameter;
receiving data generated by the at least one sensor of the fluid port, the data including a withdrawn downstream fluid volume, wherein the withdrawn downstream fluid volume is a total volume of the fluid downstream of the fluid inlet and still within the fluid channel after fluid flow through the fluid pathway is stopped; and
generating, based on sensed fluid flow information from the fluid flow sensor, a first operation modification signal to cause a flow control valve to transition to a first state when a first pre-determined volume has been delivered as measured by the fluid flow sensor, and after a pre-determined span of time, generating a second operation modification signal to cause the flow control valve to transition to a second state different than the first state.

* * * * *